United States Patent
Ban et al.

(10) Patent No.: US 9,098,861 B2
(45) Date of Patent: Aug. 4, 2015

(54) METHOD AND APPARATUS FOR CONTROLLING THE OPERATION OF A MEDICAL DEVICE

(71) Applicant: Samsung Electronics Co., Ltd., Gyeonggi-do (KR)

(72) Inventors: Dae-hyun Ban, Seoul (KR); Jae-chool Lee, Gyeonggi-do (KR)

(73) Assignee: Samsung Electronics Co., Ltd., Yeongtong-gu, Suwon-si, Gyeonggi-do (KR)

( * ) Notice: Subject to any disclaimer, the term of this patent is extended or adjusted under 35 U.S.C. 154(b) by 0 days.

(21) Appl. No.: 14/310,657

(22) Filed: Jun. 20, 2014

(65) Prior Publication Data

US 2014/0374476 A1 Dec. 25, 2014

(30) Foreign Application Priority Data

Jun. 21, 2013 (KR) .................. 10-2013-0071948

(51) Int. Cl.
*G07F 17/00* (2006.01)
*G06Q 30/02* (2012.01)
*G06F 19/00* (2011.01)

(52) U.S. Cl.
CPC .............. *G06Q 30/02* (2013.01); *G06F 19/322* (2013.01); *G06F 19/323* (2013.01); *G06F 19/3406* (2013.01)

(58) Field of Classification Search
USPC ........ 235/375, 380, 382.5, 382, 385; 705/2, 3
IPC ................ G06Q 30/02,20/342, 20/341, 10/087, G06Q 10/08; G07F 7/1008
See application file for complete search history.

(56) References Cited

U.S. PATENT DOCUMENTS

| | | |
|---|---|---|
| 7,152,785 B2 | 12/2006 | Metz et al. |
| 2006/0173713 A1 | 8/2006 | Petro et al. |
| 2011/0112856 A1 | 5/2011 | Rousso et al. |
| 2011/0125518 A1* | 5/2011 | Dhoble .............................. 705/2 |
| 2011/0125524 A1* | 5/2011 | Tenarvitz et al. ................. 705/3 |
| 2012/0109682 A1 | 5/2012 | Seltzer et al. |
| 2012/0285366 A1 | 11/2012 | Perez |
| 2014/0288947 A1 | 9/2014 | Simpson et al. |

FOREIGN PATENT DOCUMENTS

| | | |
|---|---|---|
| JP | 2003-93524 A | 4/2003 |
| KR | 10-2004-0086307 A | 10/2004 |

* cited by examiner

*Primary Examiner* — Karl D Frech
(74) *Attorney, Agent, or Firm* — Cha & Reiter, LLC

(57) ABSTRACT

A method for controlling a medical device is provided including: acquiring identification information of a patient; acquiring patient information and diagnostic information based on the identification information; and changing a state of the medical device based on the patient information and the diagnostic information.

30 Claims, 26 Drawing Sheets

FIG. 7

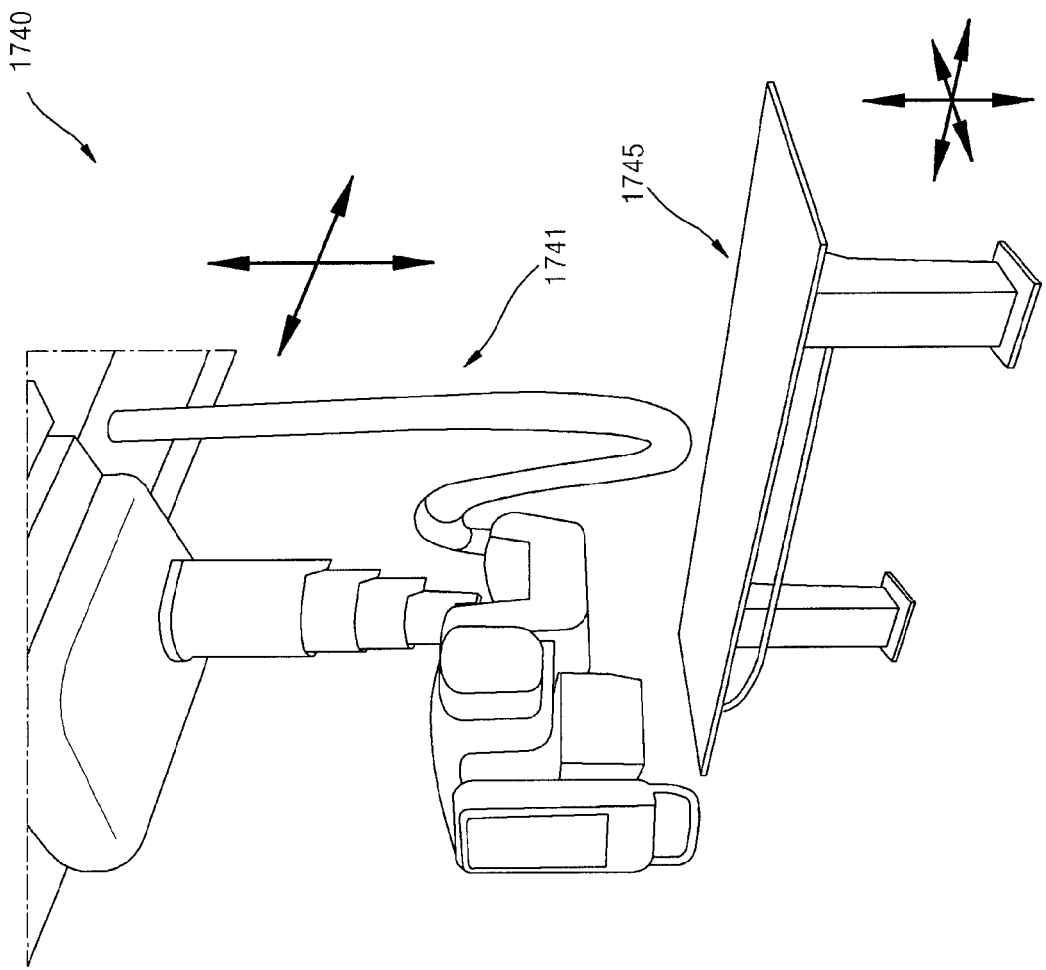
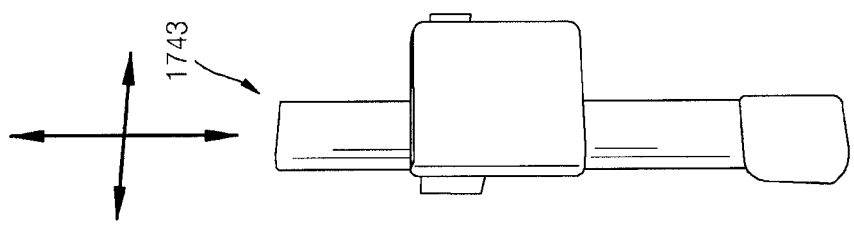
FIG. 16D

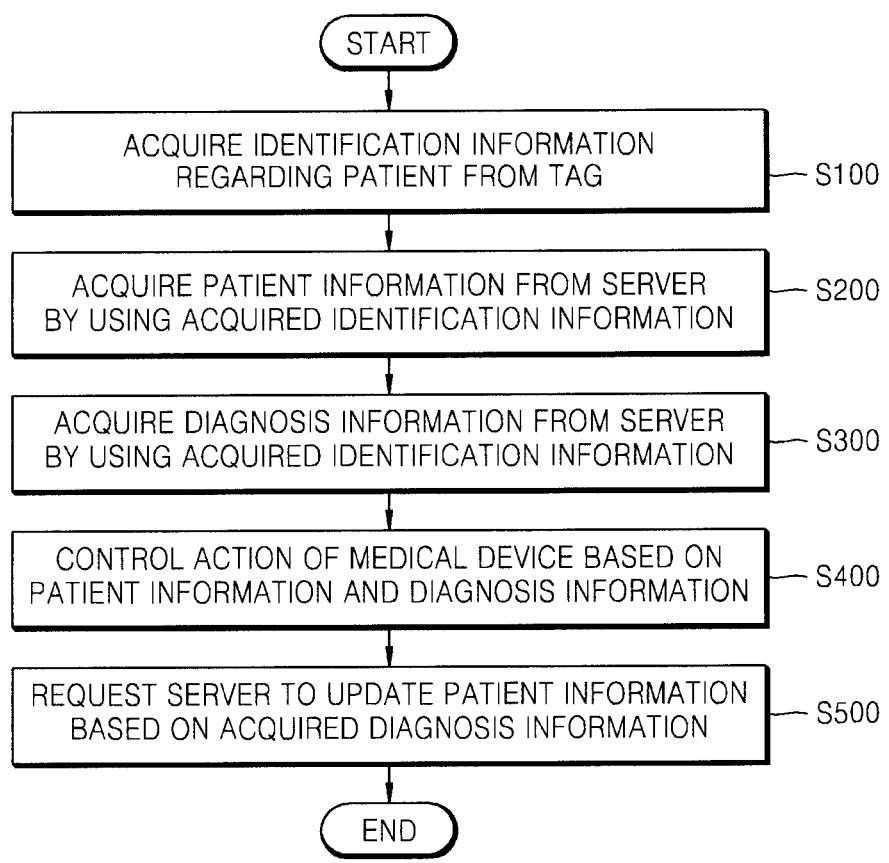

METHOD AND APPARATUS FOR CONTROLLING THE OPERATION OF A MEDICAL DEVICE

CROSS-REFERENCE TO RELATED PATENT APPLICATION

This application claims the benefit of Korean Patent Application No. 10-2013-0071948, filed on Jun. 21, 2013, in the Korean Intellectual Property Office, the disclosure of which is incorporated herein in its entirety by reference.

BACKGROUND

1. Field of the Disclosure

The present disclosure relates to medical devices and in particular to a method and apparatus for controlling the operation of a medical device.

2. Description of the Related Art

Medical diagnosis devices include ultrasound diagnosis devices, X-ray imaging devices, computerized tomography (CT) devices, magnetic resonance imaging (MRI) devices, and various other types of devices.

Ultrasound diagnosis devices acquire images of an object's interior (e.g., tomography of soft tissues or blood flow) by irradiating the object with ultrasound signals generated by transducers of a probe to and receiving echo signals reflected by the object. Ultrasound diagnosis devices may be used for detection of foreign substances, damage check, and various other medical purposes.

CT imaging devices produce precise tomography images of objects by obtaining and processing tens or hundreds of X-ray images of the objects. By doing so, the CT imaging devices may produce 2D or 3D images of the interior structure of the objects.

MRI imaging devices use magnetic resonance imaging to produce images of the external structure of objects. MRI imaging provides higher resolution and contrast than other imaging techniques. Furthermore, MRI imaging causes no radiation exposure and is thus safer to human body than X-ray imaging. And still furthermore, MRI permits the capture of axial images, sagittal images, and coronal images without relocating the object that is being examined.

SUMMARY

The present disclosure provides an apparatus for controlling an action of a medical device using patient information and diagnostic information. According to one aspect of the disclosure, a method for controlling a medical device is provided comprising: acquiring identification information of a patient; acquiring patient information and diagnostic information based on the identification information; and changing a state of the medical device based on the patient information and the diagnostic information.

According to another aspect of the disclosure, an apparatus for controlling a medical device, the apparatus comprising: an identification information acquiring unit for acquiring identification information of a patient from a tag; a patient information acquiring unit for acquiring patient information from a server, the patient information being acquired based on the identification information; a diagnostic information acquiring unit for acquiring diagnostic information for the patient from the server, the diagnostic information being acquired based on the identification information; and a control unit for changing a state of the medical device based on the patient information and the diagnostic information.

BRIEF DESCRIPTION OF THE DRAWINGS

The above and other features and advantages of the present disclosure will become more apparent by describing in detail exemplary embodiments thereof with reference to the attached drawings in which:

FIG. 7 is a diagram of an example of a patient information record according to aspects of the disclosure;

FIG. 16A, FIG. 16B, FIG. 16C, and FIG. 16D are diagrams illustrating examples different changes of state that a medical device can undergo based on the patient information and/or the diagnostic information, according to aspects of the disclosure;

FIG. 17 is a flowchart of an example of a process for updating patient information according to aspects of the present disclosure;

DETAILED DESCRIPTION OF THE DISCLOSURE

Figure 1:
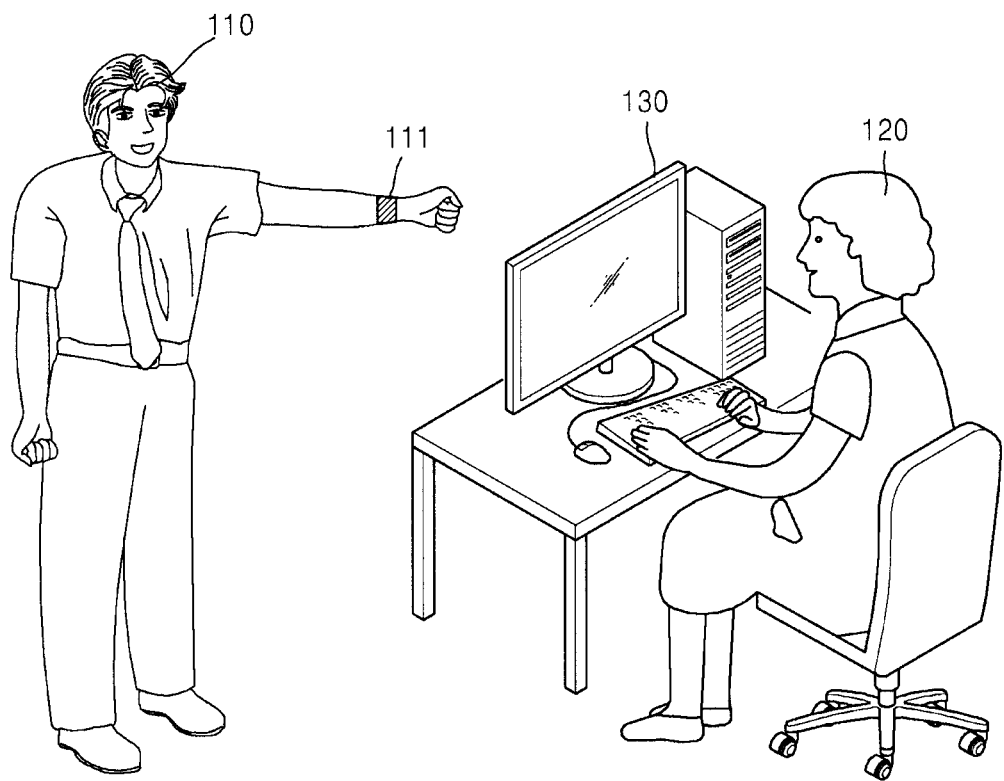
FIG. 1 is a diagram illustrating a process for diagnosing patients that is known in the prior art.

Aspects of the present disclosure will now be described more fully with reference to the accompanying drawings. The examples provided throughout the disclosure should not be construed as being limited to the embodiments set forth herein; rather, these examples are provided for illustrative purposes only.

It is to be understood that the meaning of the terms used herein should be interpreted in light of the specification.

The term "unit" used in the present specification may refer to a component that is implemented (e.g., executed) using hardware (e.g., a circuit, an integrated circuit, etc.). For example, the term "unit" may refer to a logical component that is implemented using hardware (e.g., executed by a processor). The term "image" herein may refer to data consisting of discrete image elements (e.g., pixels in a 2D image and voxels in a 3D image). For example, the term image may include medical images obtained by using an X-ray imaging system, a computer tomography (CT) imaging system, a magnetic resonance imaging (MRI) system, an ultrasound wave imaging system, and any suitable type of medical imaging system. Furthermore, in the present specification, the term "object" may refer to a person or an animal, or a part of a person or an animal. For example, the object may include the liver, the heart, the womb, the brain, a breast, the abdomen, or a blood vessel of a person. Additionally or alternatively, the "object" may refer to a phantom. The phantom could be an entity that is at least partially composed of a material having at least one property that is similar to a property of a human body. Furthermore, the term "user" herein may refer to a medical expert including a doctor, a nurse, a medical technician, a medical imaging expert, and a medical device repairman. However, the term is not limited thereto.

The present disclosure will now be described more fully with reference to the accompanying drawings, in which specific examples are shown. It is to be understood that these examples are non-limiting and various other examples can be conceived by those of ordinary skill in the art after reading the present disclosure. Like reference numerals in the drawings denote like elements.

FIG. 1 is a diagram illustrating a process for diagnosing patients that is known in the prior art. According to the process, a user 120 diagnoses a patient 110. As shown in FIG. 1, the user 120 obtains information of the patient 110 by reading barcodes from the patient's bracelet 111 and diagnoses the patient by using an assisting device 130 for diagnosis, such as a computer.

In some instances, the user 120 may manually operate a medical device to examine the patient. In such instances, the user 120 may determine various configuration settings of the medical device, such as an optimal imaging protocol for acquiring an optimal ultrasound image, an X-ray image, or a MRI image of a patient. The user 120 may determine these settings based on the user's own knowledge and experience. Furthermore, the user 120 may manually adjust the positions of various components of the medical device. For example, if the medical device is an X-ray scanner, the user 120 may manually move an X-ray source to a portion of the patient 110 that is to be scanned. Furthermore, the user may adjust the position of a table on which the patient 110 lies.

Figure 2:
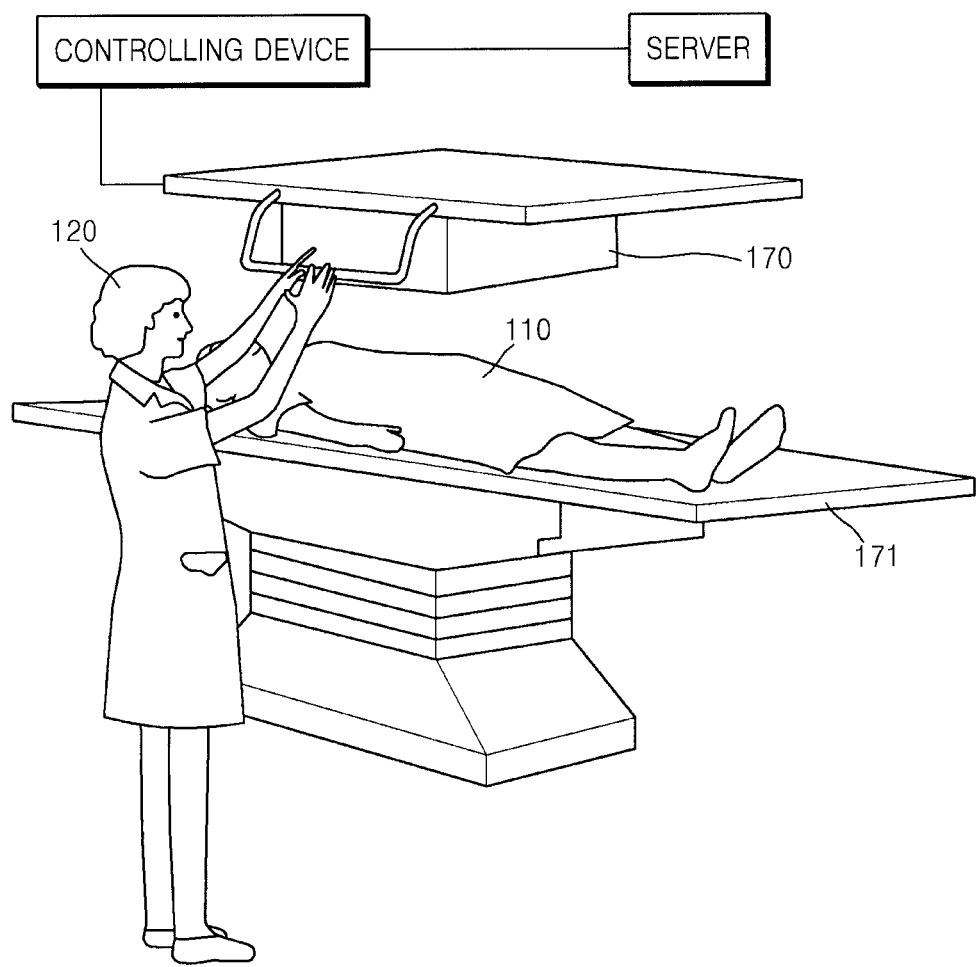
FIG. 2 is a diagram illustrating an example of the operation of a medical device according to aspects of the disclosure.

FIG. 2 is a diagram illustrating an example of the operation of a medical device according to aspects of the disclosure. According to this example, a patient 110 is examined using a medical device 1700. The medical device may be an X-ray imaging device, an ultrasound imaging device, a CT imaging device, an MRI device, and/or any other suitable type of medical device.

The patient 110 is provided with an object recognizing unit 1100. The object recognizing unit 1100 may include a patient bracelet, a card, and a badge including RFID chips, and or any other carrier of patient information. The medical information regarding a patient may include any suitable type of information related to the patient. For example, the medical information may include personal information regarding the patient, such as name, gender, height, and weight of the patient, information regarding medical history of the patient, and information regarding diagnosis history of the patient. Additionally or alternatively, the medical information may include information regarding diagnosis (or order) of a doctor regarding a current illness of a patient.

Controlling device 1500 may control the operation of the medical device 1700. The controlling device 1500 may include an RF reader or any other suitable hardware for acquiring identification information of the object from the object recognizing unit 1100. When the identification is acquired, the controlling device 1500 may acquire medical information regarding the patient from a server 1600. Afterwards, the controlling device 1500 may control the operation of the medical device 1700 based on the medical information acquired from the server 1600. For example, the controlling device 1500 may configure an imaging environment of the medical device based on the acquired information (e.g., configure an imaging mode suitable for diagnosing an object) or output an alert indicating that the medical device 1700 is not suitable for the patient (e.g., because the patient is at a high risk of cancer).

Figure 3:
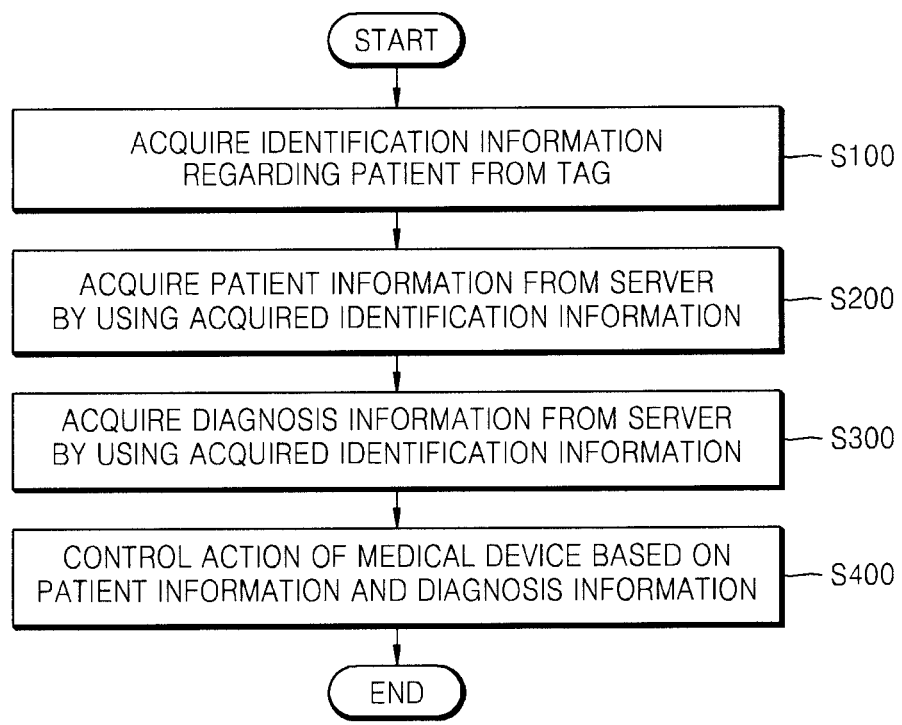
FIG. 3 is a flowchart of an example of a process for controlling the operation of a medical device according aspects of the present disclosure.

FIG. 3 is a flowchart of an example of a process for controlling the operation of a medical device according aspects of the present disclosure. At operation S100, identification information of the patient is acquired from a tag. At operation S200, patient information is acquired from a server by using the acquired identification information. At operation S300, diagnostic information is acquired from a server by using the acquired identification information. At operation S400, the medical device is caused to perform an action based on the patient information and the diagnostic information.

According to aspects of the present disclosure, identification information regarding a patient can be acquired via a patient recognizing device, such as a tag. Patient information and diagnostic information corresponding to the identification information regarding the patient can be acquired from a server. In this way, the operation of the medical device may be controlled based on the patient information and the diagnostic information.

Figure 4:
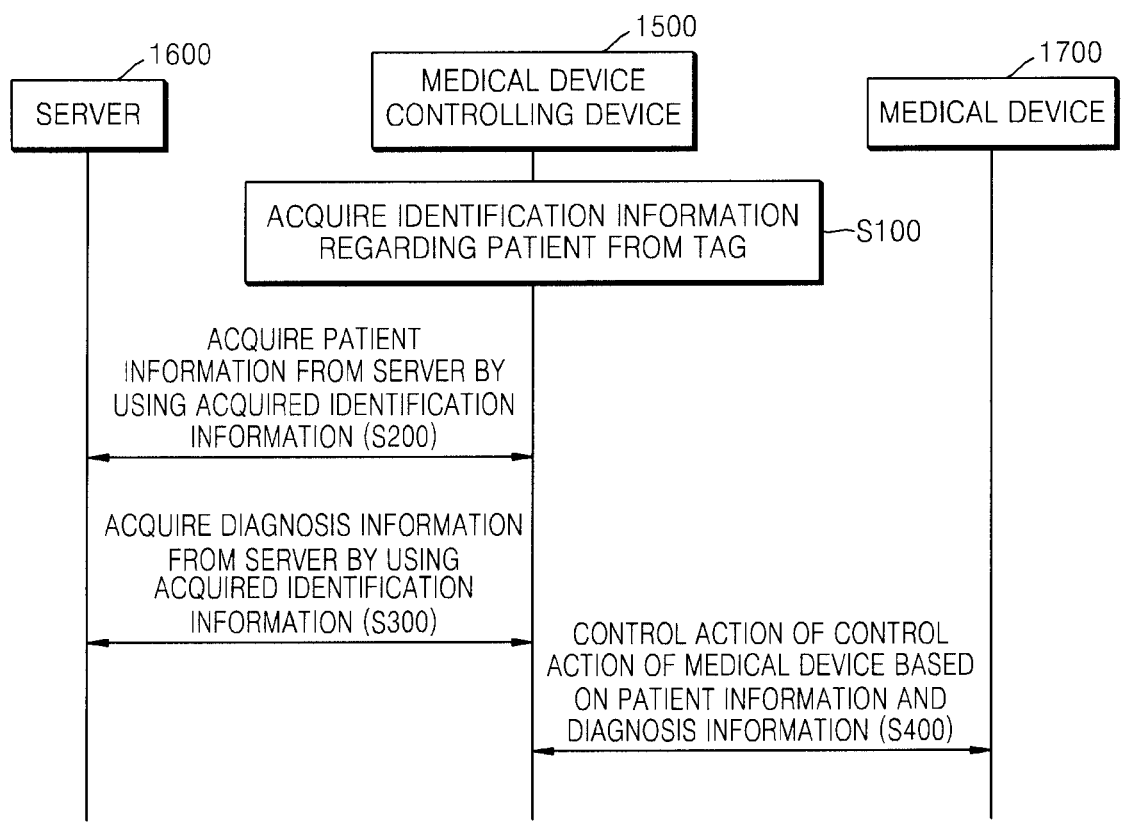
FIG. 4 is flowchart illustrating an example of an implementation of the process of FIG. 3.

FIG. 4 is flowchart illustrating an example of an implementation of the process of FIG. 3. In this example, the controlling device 1500 may acquire identification information regarding a patient from a tag (operation S100). Furthermore, the controlling device 1500 may acquire patient information from the server 1600 by using the acquired identification information (operation S200). Furthermore, the controlling device 1500 may acquire diagnostic information from the server 1600 by using the acquired identification information (operation S300). Furthermore, the controlling device 1500 may change the state of the medical device 1700 based on the patient information and the diagnostic information (operation S400).

Patient information according to aspects of the present disclosure may include personal information regarding a patient, such as name, age, gender, body measures (e.g., height, weight, blood type, etc.), and nationality of a patient. Furthermore, the patient information may include information regarding diagnosis history of a patient, such as dates, names, and results of previous diagnosis (or medical tests) of the patient. Furthermore, the patient information may include information regarding current state of a patient, e.g., current symptoms of the patient.

The diagnostic information according to aspects of the present disclosure may include a diagnosis record, a prescription, and/or any other suitable record that is produced over the course of managing the patient's health.

FIGS. 5A-D are diagrams providing examples of different tags according to aspects of the present disclosure. The tags, as discussed above, may be capable of performing close-distance communication. As illustrated by this example, the tags may be embodied in various forms including a bracelet, a clip, a medical card, etc.

Figure 5A:
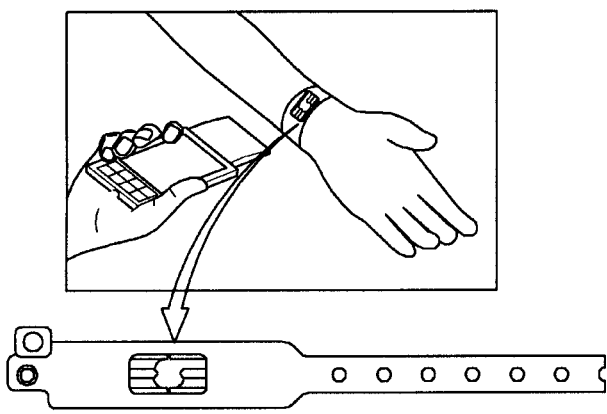
FIG. 5A, FIG. 5B, FIG. 5C, and FIG. 5D are diagrams providing examples of different tags according to aspects of the present disclosure.
Figure 5B:
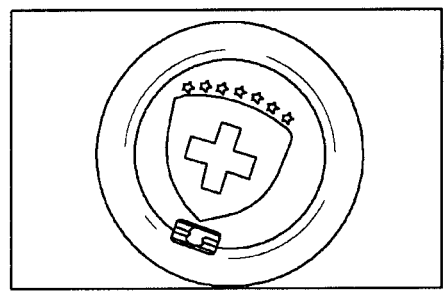
Figure 5C:
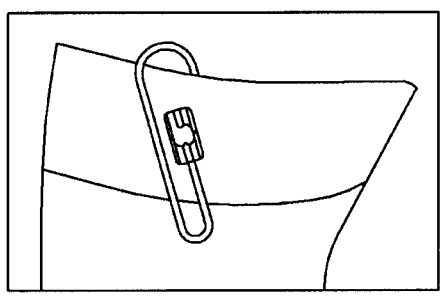
Figure 5D:
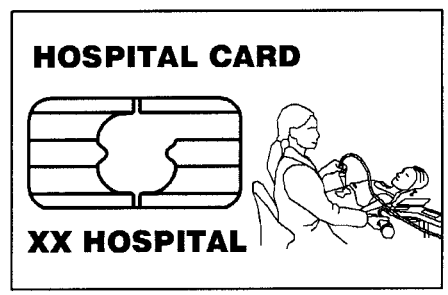

For example, as shown in FIG. 5A, a tag may be integrated into a medical bracelet including a chip capable of performing close-distance communication (e.g., an RFID chip). As another example, as shown in FIG. 5B, a patient's tag may be integrated in a badge. As yet another example, as shown in FIG. 5C, the tag may be integrated into a clip. Furthermore, as shown in FIG. 5D, the tag may be integrated into a medical card.

In operation, a patient wearing a tag-integrated article (e.g., a bracelet, clip, badge, etc.) can provide information regarding him or her to a user of a medical device by positioning the tag-integrated article towards a receiver device, such as a standalone receiver device or one that is integrated into the controlling device 1500. As noted above, the tag may include hardware capable of performing wireless communications via close-distance communication protocols, such as Wi-Fi, Bluetooth, Zigbee, Wi-Fi Direct (WFD), ultra wideband (UWB), or infrared data association (IrDA), and/or any other suitable type of protocol. This hardware may be operable to provide the patient's identification information to the receiver. The present disclosure is not limited to any specific type of tag.

For example, if a patient is a child or a foreigner who is unable to smoothly communicate with a user of a medical device, the user of the medical device may easily acquire patient information by using a bracelet, a badge, or a clip as described above, compared to the related art. For instance, when a patient wearing a bracelet enters a diagnosis room, the controlling device 1500 may recognize the patient via a close-distance communication with the chip included in the bracelet, badge, or clip. Furthermore, the controlling device 1500 may acquire identification information regarding the patient via a close-distance communication with a chipset included in the bracelet.

Figure 6:
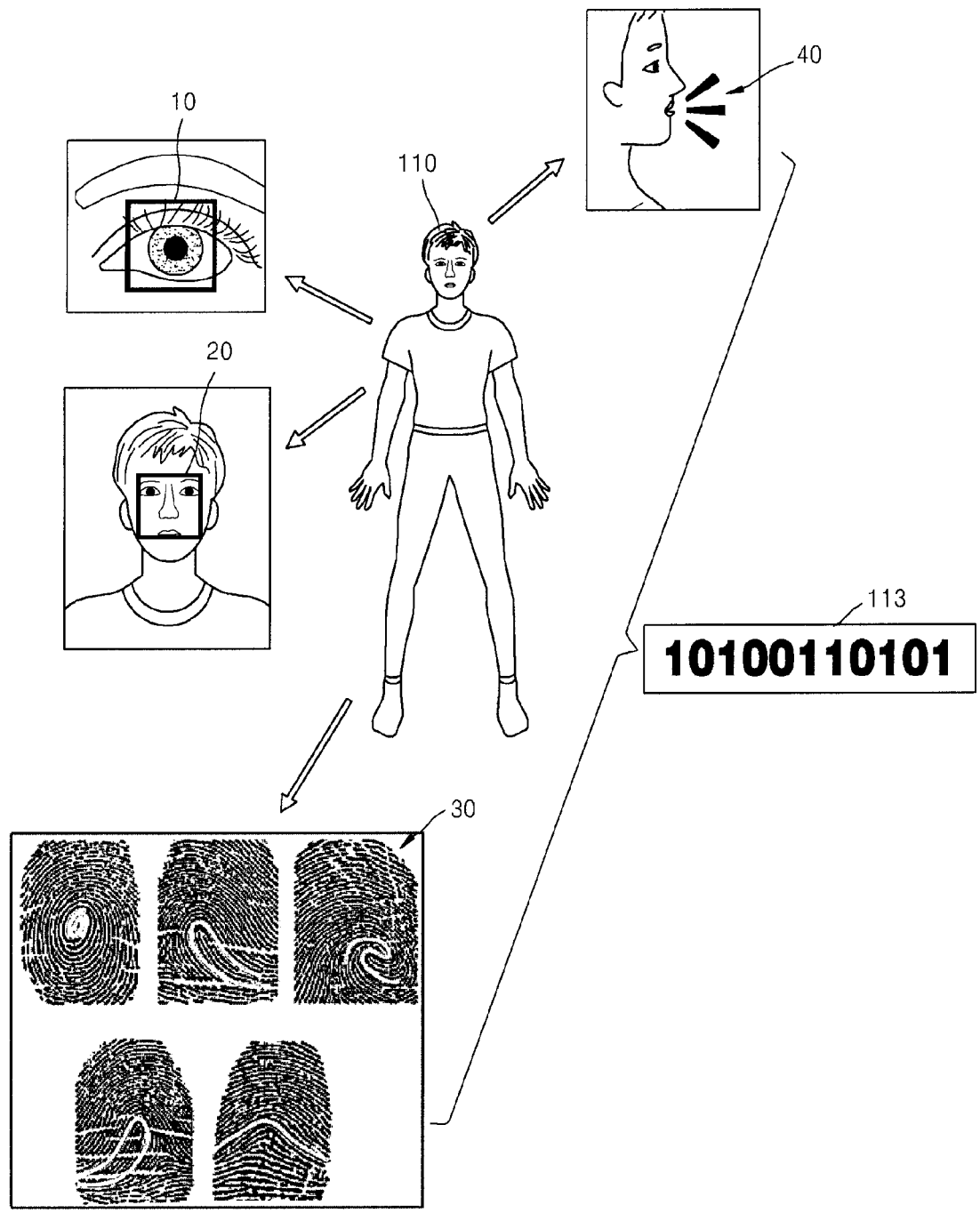
FIG. 6 is a diagram illustrating an example of alternative means for obtaining identification information of a patient.

FIG. 6 is a diagram illustrating an example of alternative means for obtaining identification information of a patient. For example, the identification may be obtained based on at least one of the patient's iris, face, fingerprint, and voice. The identification information may be generated with respect to each patient in advance. The identification information according to aspects of the present disclosure may be generated as at least one from among characters, numbers, barcodes, and QR codes.

As illustrated, the identification information of a patient may be obtained by using iris information 10 of a patient 110. Iris recognition may include a technique for recognizing an object by using an iris pattern. An iris pattern is a circular pattern protruding nearby a pupillary and is unchanged in one's lifetime once set at one's birth. Furthermore, shapes of iris patterns vary from one individual to another. Such an iris pattern includes about 1078 unique patterns. Therefore, various feature variables for recognizing an iris may be set. Furthermore, a biologically completed iris pattern does not change, and an iris image may be acquired without any direct contact.

Furthermore, identification information according to aspects of the present disclosure may be generated by using face information 20 of the patient 110.

Face recognition may include a technique for confirming identity of a target person by storing face images of target persons in a database in advance and comparing such a pre-existing face images to a face image of a target person acquired via a camera (not shown). To detect a face from an input image, a knowledge-based method for detecting a face based on knowledge of a researcher (or an image analyst), a feature-based method for detecting a face based on face features, or a template-matching method for detecting a face by comparing an input image to standard templates that are generated in advance may be used in a face detecting operation.

In a face recognizing operation, main components including eyes, nose, eyes, and mouth of a face detected by using a method as described above may be determined, and then a face may be recognized based on unique features of a target person (e.g., distance between eyes, width of a nose, height and shape of cheekbone, ratios of width and height of forehead in a face, etc.).

Furthermore, identification information according to aspects of the present disclosure may be generated by using fingerprint information 30 of the patient 110. Fingerprint recognition is a technique for determining identification of a target person having an input fingerprint by comparing the input fingerprint to fingerprint data that is input in advance, where positions and properties of feature points including bifurcation points, end points, core points, and deltas of fingerprint ridges of target persons are extracted and stored as the fingerprint data in advance.

Furthermore, identification information according to aspects of the present disclosure may be generated by using voice information 40 of the patient 110. Voice recognition may include a technique for detecting information related to the most similar voice from voice database that is established in advance by extracting features from voices of target persons transmitted to a computer or a voice recognition system via a telephone or a microphone and analysing the extracted features.

Voice recognition is a type of pattern recognition. Since voices, pronunciations, and intonations differ from one person to another, voice features are extracted and stored as voice data in advance, and identification of a person is recognized by comparing an input voice to the stored voice data. Voice features may include vocal track characteristics that are determined based on patterns including lip shapes, tongue positions, energy change patterns, etc. According to aspects of the present disclosure, information for recognizing a patient may be generated based on vocal track characteristics that are determined based on patterns including lip shapes, tongue positions, energy change patterns, etc.

As described above, identification information of a patient may be generated as at least one from among characters, numbers, barcodes, and QR codes based on at least one from among iris, face, fingerprint, and voice data of a patient. However, the present disclosure is not limited thereto.

The identification of a patient may include a combination of at least one of numbers, characters, and other symbols, such as 10100110101. Furthermore, identification information may include a combination of characters and numbers. Furthermore, the identification information may be encrypted according to a predetermined encryption algorithm According to one specific implementation, only the identification information of a patient may be included in a tag, and patient information and diagnostic information may be stored and managed separately. In other words, by storing patient information including personal information of a patient and diagnostic information including a doctor's prescription in a separate storage (e.g., a server) other than a tag and accessing the patient information and the diagnostic information, data security problems may be quickly handled.

Furthermore, since medical information regarding a patient may be jointly managed according to aspects of the present disclosure, each hospital may save costs on data management. In other words, according to aspects of the present disclosure, since medical information regarding a patient (e.g., patient information and diagnostic information) is jointly managed by using a server and is shared by hospitals, even if a patient uses a new hospital other than a hospital the patient has previously used, medical history of the patient may be conveniently accessed by the new hospital, thus enabling the patient to be diagnosed by the new hospital.

The server according to aspects of the present disclosure may include (or be part of) a picture archiving and communication system (PACS), an electronic medical record (EMR) system, a personal health record (PHR) system, and a radiology information system (RIS), and/or any other suitable record management system. The server according to aspects of the present disclosure may be located inside or outside a hospital. Furthermore, the server may be connected to other devices, such as medical devices, over any of a wired connection and a wireless connection. Furthermore, the server according to aspects of the present disclosure may include a cloud server. For example, the cloud server may include a public cloud server, a private cloud server, and a home PC.

As described above, medical information regarding a patient (e.g., patient information and diagnostic information) may be stored and managed on a server in association with the identification information of the patient. A user of a medical device may request the server to provide medical information regarding the patient, receive the medical information regarding the patient from the server, and use the medical information regarding the patient for diagnosis of the patient. The availability of the medical information permits the making of a more precise diagnosis than otherwise. Furthermore, since medical information regarding a patient (e.g., patient information and diagnostic information) may be jointly managed by a server and shared by hospitals, the patient may switch hospitals more easily.

Figure 7:
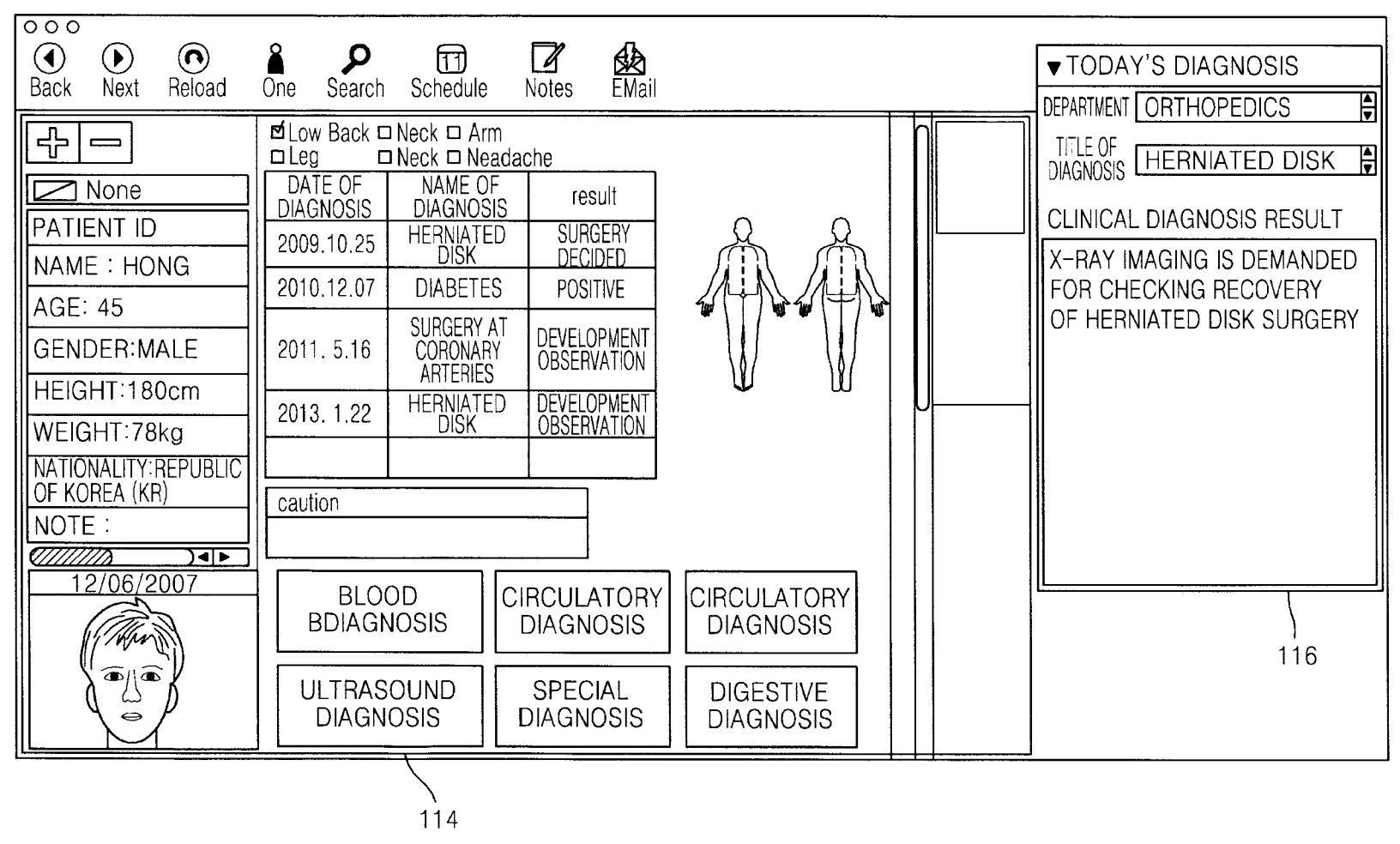

FIG. 7 is a diagram of an example of a patient information record according to aspects of the disclosure. The record may include patient information 114 and diagnostic information 116. Patient information 114 according to aspects of the present disclosure may include personal information regarding a patient, such as name, age, gender, body measures (e.g., height, weight, blood type, etc.), and nationality of a patient. Furthermore, the patient information 114 may include information regarding diagnosis history of a patient, such as dates, names, and results of previous diagnosis of the patient. Furthermore, the patient information 114 may include information regarding current state of a patient, e.g., current symptoms of the patient. The diagnostic information 116 according to aspects of the present disclosure may include doctor order information, such as information regarding doctor's diagnosis and information regarding a doctor's prescription.

Figure 18:
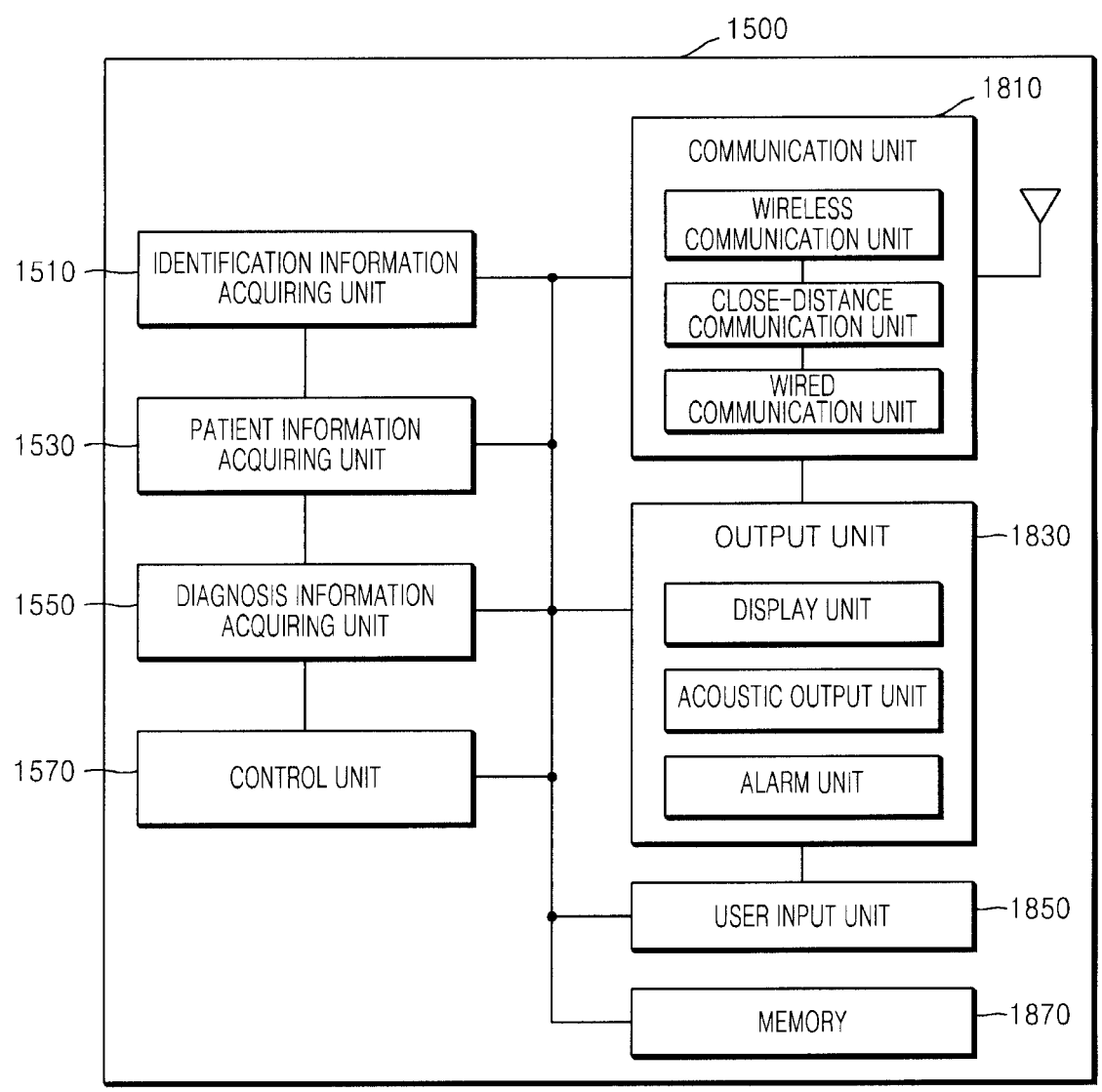
FIG. 18 is a diagram of an example of a controlling device, according to aspects of the present disclosure.

For example, as shown in FIG. 7, personal information and information regarding diagnosis history related to a patient Hong, Gil-Dong may be provided to a user as the patient information 114 via an output unit 1830 (shown in FIG. 18). As indicated by the diagnostic information 116, the patient Hong, Gil-Dong has been recently prescribed an X-ray imaging in order to determine his recovery from a herniated disk surgery.

Disk herniation is a medical condition affecting the spine in which a tear in the outer, fibrous ring of an intervertebral disc allows the soft, central portion to bulge out beyond the damaged outer rings. To check and diagnose a herniated disk, myleography, CT imaging, and MRI imaging may be utilized. Although myleography is a very effective method for diagnosing a herniated disk, it is necessary to inject a contrast agent into the spine, and thus CT imaging and MRI imaging are more preferred these days. In a CT image, an intervertebral disk is indicated with darker contrast than a spinal canal and is distinguished from fat, thus enabling a highly accurate diagnosis. Furthermore, in an MR image, a degenerative change, swelling, and herniation of an intervertebral disk may be easily recognized due to clear contrast difference between intervertebral disks and fat.

As shown in the example of FIG. 7, the patient Hong, Gil-Dong has been prescribed an X-ray imaging. Based on the diagnostic information 116, the patient Hong, Gil-Dong needs to get an X-ray imaging (e.g., CT imaging). However, certain complications may arise if the patient Hong, Gil-Dong is allergic to a particular contrast agent used for the medical imaging.

According to aspects of the present disclosure, medical information regarding a patient, name of disease, and cautions for using medical devices may be coded by using characters and numbers, and thus medical information regarding the patient may be used by a user of a medical device more quickly and efficiently. The cautions for using medical devices may include any suitable type of information relating to the patient's suitability to be examined with a particular medical device. By way of example, the cautions for using medical devices may include an indication of a medical condition that could make it unsafe for the patient to be examined with a particular medical device. As is discussed further below, the cautions may be organized according to different types of medical devices. Thus, for each available type of medical device different types of pertinent medical conditions may be identified.

In some implementations, since data regarding medical histories of patients may be massive, names of diseases may be coded for effective management of medical history data and cautions for using respective medical devices (e.g., medical history of a patient that needs to be checked before medical imaging) may be generated in advance. When pre-set codes included in the medical information of a patient match codes associated with alerts for using medical devices regarding the patient, the alerts may be output. For example, messages such as "the patient to be diagnosed has previously received an arterial surgery," may be provided to a user of a medical device, thereby notifying the user that the patient might be put at risk by the user of the medical device.

In other words, according to aspects of the present disclosure, by providing cautions for using medical devices regarding a patient that may match coded medical information regarding the patient to a user of a medical device, safer and more precise diagnosis may be performed regardless of the experience or expertise of the user of the medical device.

Figure 8:
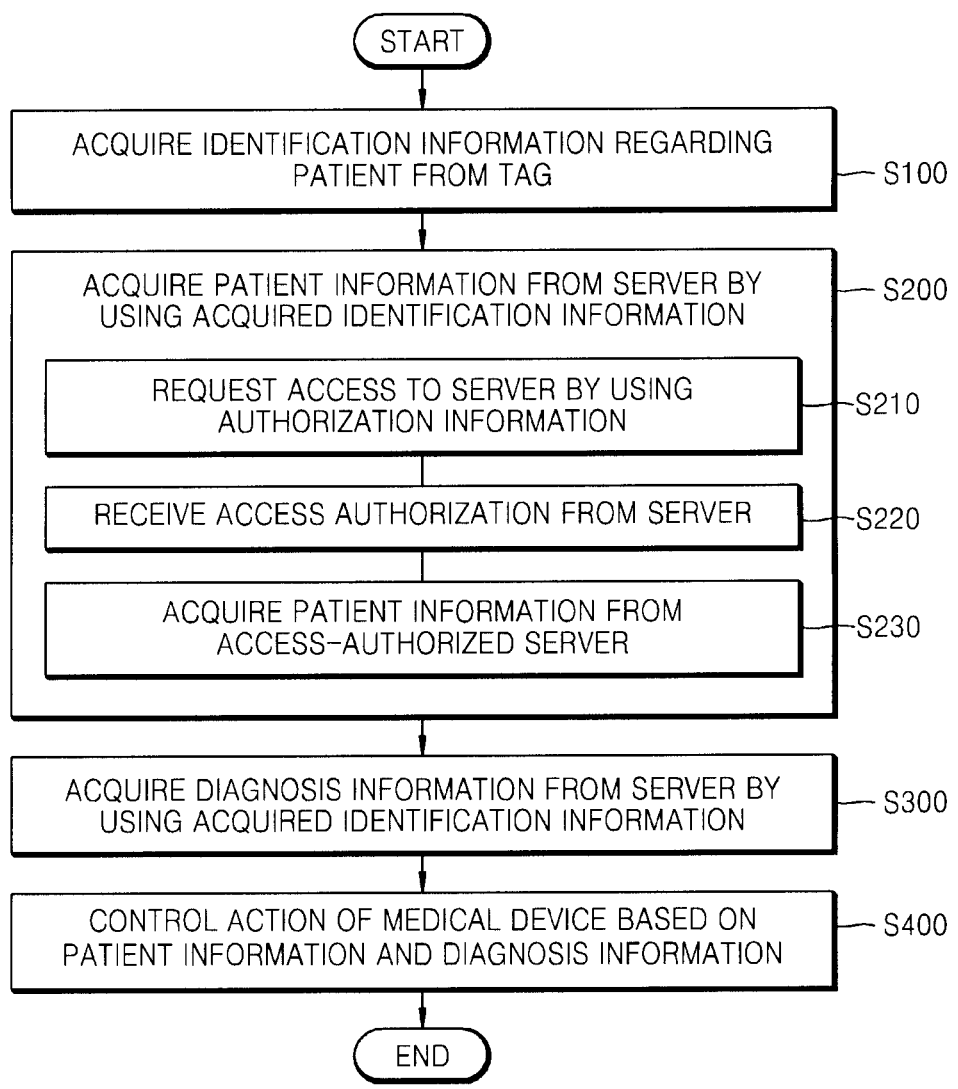
FIG. 8 is a flowchart illustrating an example of a process for performing operation S200 of the process of FIG. 3.

FIG. 8 is a flowchart illustrating an example of a process for performing operation S200 of the process of FIG. 3. An operation S210, access is requested from a server by using authorization information. At operation S220 access authorization is received from the server. At operation S230, patient information is acquired from the access-authorized server.

Figure 9:
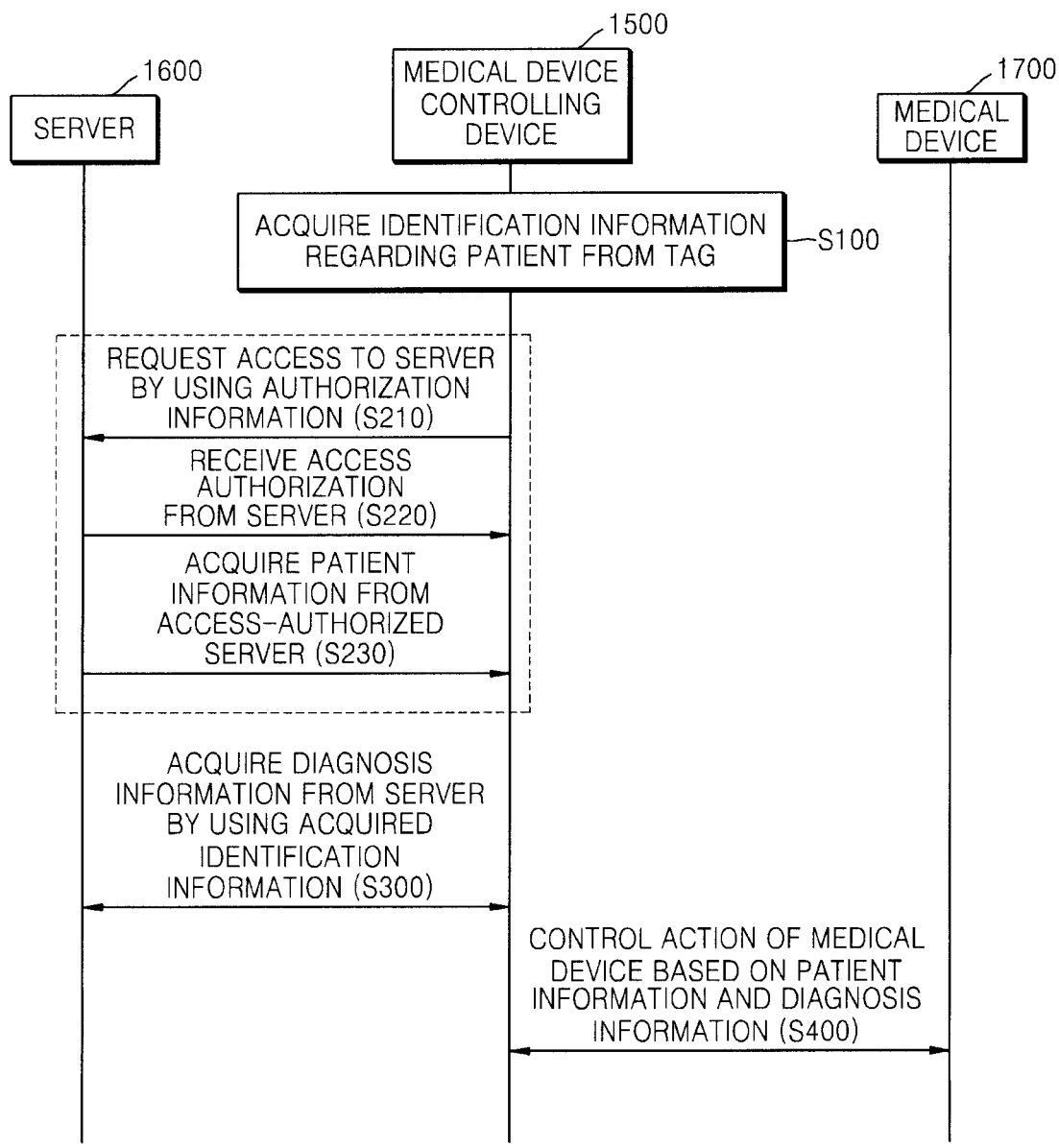
FIG. 9 is a flowchart illustrating an example of an implementation of the process of FIG. 8.

FIG. 9 is a flowchart illustrating an example of an implementation of the process of FIG. 8. According to the process, the controlling device 1500 may request an access to the server 1600 by using acquired authorization information (operation S210). Furthermore, the controlling device 1500 may receive an access authorization from the server 1600 via a predetermined authorization process (operation S220). When the access authorization is received, the controlling device 1500 may acquire patient information from the server 1600 (operation S230).

According to aspects of the present disclosure, medical information regarding a patient may be jointly managed by a server, a user may request an access to the server by using authorization information included in the identification information (operation S210).

The server may verify validity of the authorization information, and, if the authorization information is valid, the server may authorize an access. In other words, an access authorization may be received from a server by using valid authorization information (operation S220). However, if the authorization information is not valid, the server may demand the input of valid authorization information. Furthermore, if the authorization information is not valid and the number of attempts for inputting the authorization information exceeds a predetermined number of times (e.g., more than 3 times), the server may ban an access of the corresponding user for a predetermined period of time (e.g., 1 hour to 6 months). However, the present disclosure is not limited thereto. The authorization process may be performed by a separate authorization server (not shown) connected to the server 1600 or by an authorization module in the server 1600. When an access to the server 1600 is authorized, patient information corresponding to identification information may be acquired (operation S230).

In one specific implementation, the patient's tag may store the minimum information for recognition of the patient 110 (e.g., identification information) in a tag 1100 and may allow the server 1600 inside or outside a hospital to manage medical information regarding the patient 110, thereby improving convenience of managing medical information regarding the patient. Furthermore, by utilizing authorization information as described above, possible security risks can be reduced during data transmission and reception between the user 120 and the server 1600 or between the patient 110 and the server 1600. Furthermore, a user may quickly and precisely diagnose a patient by using medical information regarding the patient that is managed and provided by the server 1600.

Figure 10:
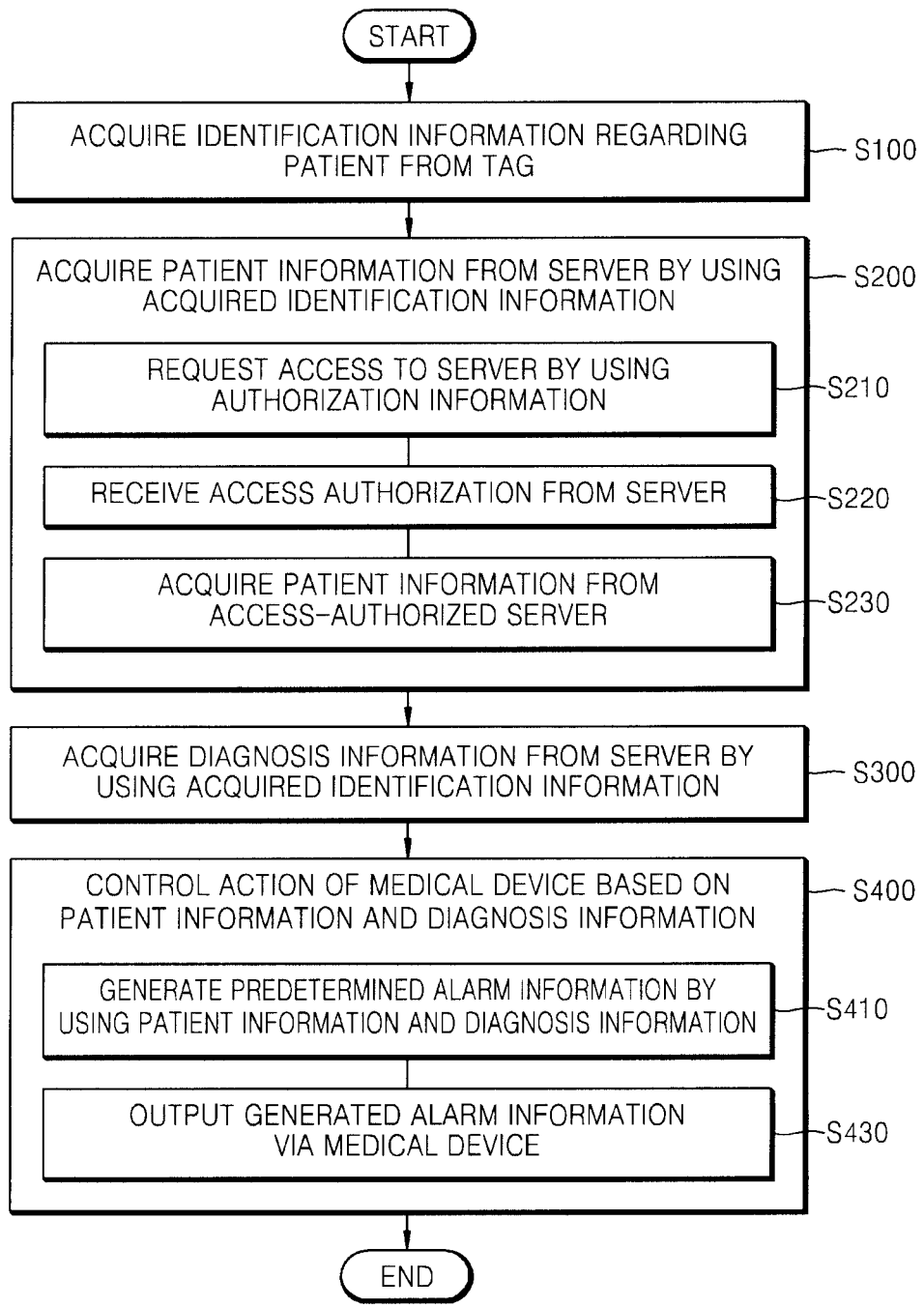
FIG. 10 is a flowchart illustrating an example of a process for performing operation S400 of the process of FIG. 3.

FIG. 10 is a flowchart illustrating an example of a process for performing operation S400 of the process of FIG. 3. At operation S410, predetermined alarm information is generated based on the patient information and the diagnostic information. At operation S430 the generated alarm information is output by a medical device. The alarm information may include cautions according to the type of medical device that is to be used (e.g., ultrasound imaging device, MRI device, CT scanner, and X-ray imaging device). The alarm information may include, sound, text, images, and/or any other suitable type of media.

Figure 11:
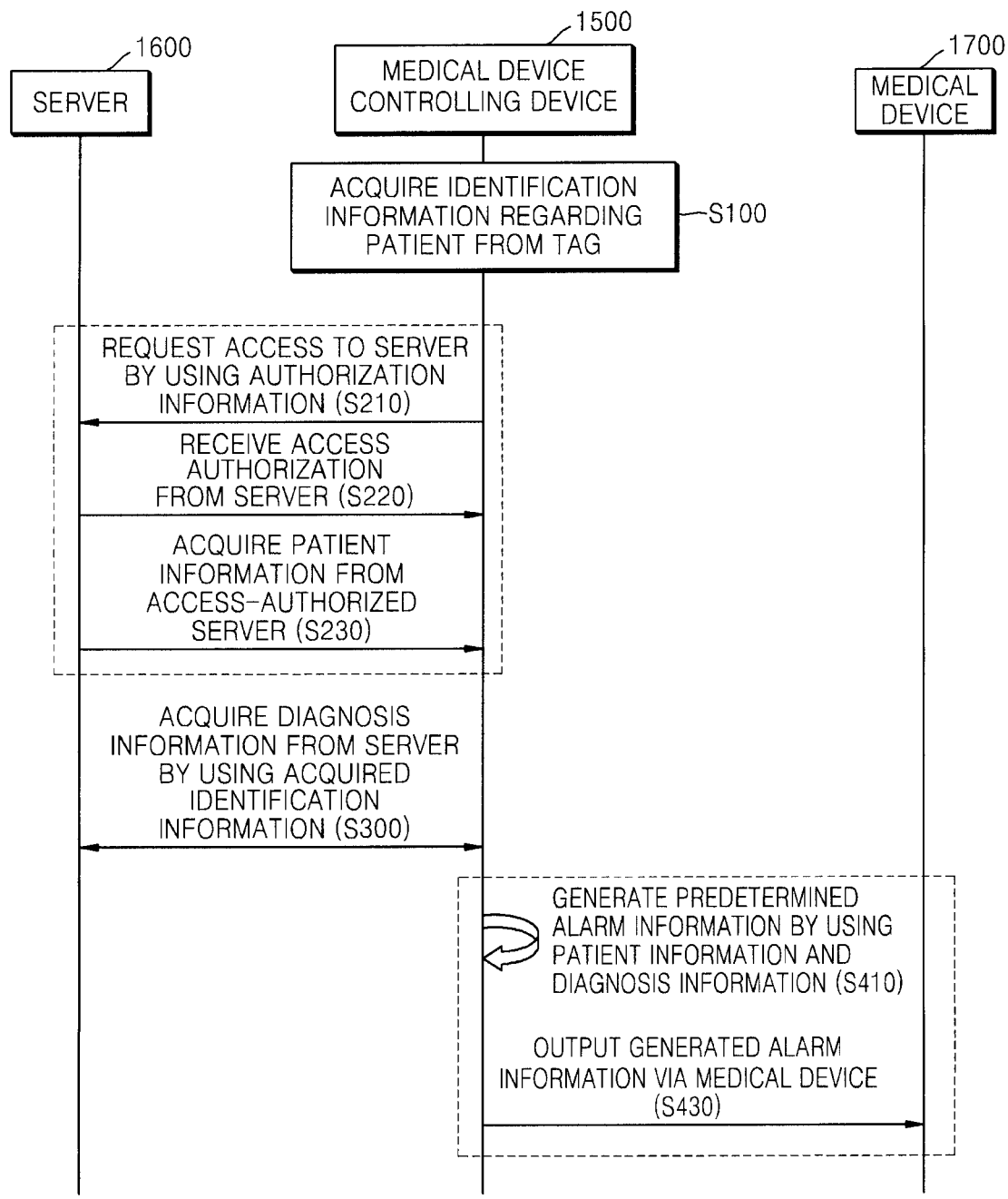
FIG. 11 is a flowchart illustrating an example of an implementation of the process of FIG. 10.

FIG. 11 is a flowchart illustrating an example of an implementation of the process of FIG. 10. According to the example, the controlling device 1500, may generate alarm information by based the patient information and diagnostic information that is obtained from the server 1600 (operation S410). Furthermore, the controlling device 1500 may control the medical device 1700 to output generated alarm information via the medical device (operation S430).

Figure 12A:
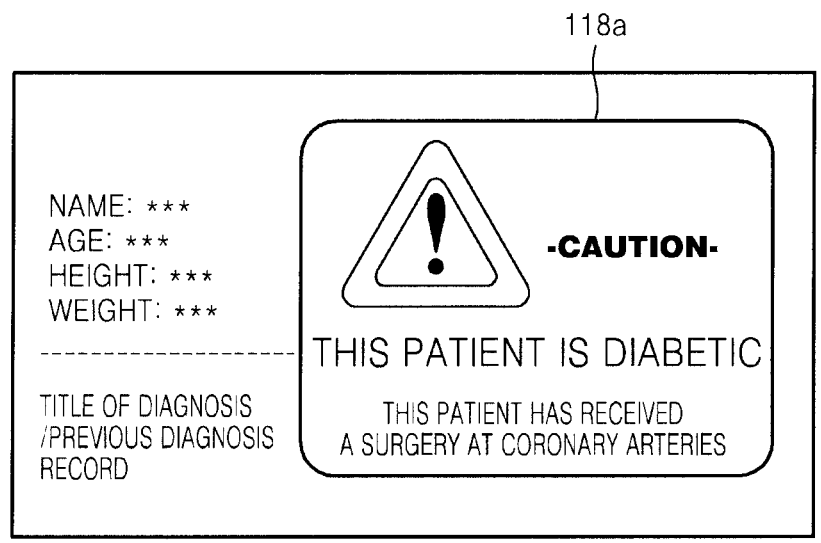
FIG. 12A, FIG. 12B, and FIG. 12C are diagrams illustrating different examples of alarm information according to aspects of the present disclosure.
Figure 12B:
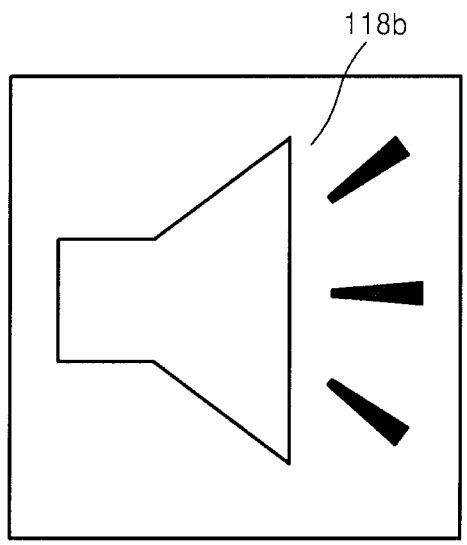
Figure 12C:
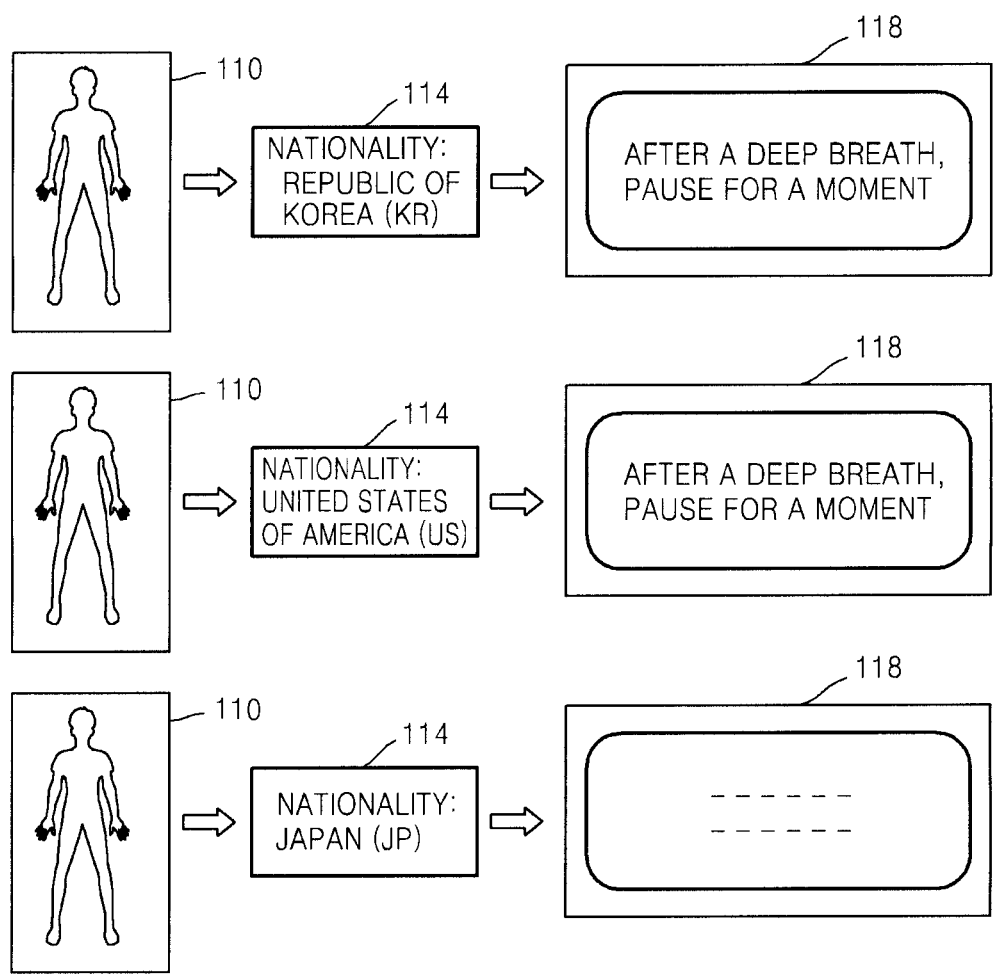

FIGS. 12A-C are diagrams illustrating different examples of alarm information according to aspects of the present disclosure. As shown in FIG. 12A, alarm information 118a may include an indication of a previous diagnosis of the patient For example, in case of performing MRI imaging, it may be difficult to perform MRI imaging to a patient who has previously received heart surgery or arterial surgery. In other words, it is necessary for a user to identify past medical history of the patient before examining the patient with a given medical device.

Omission to identify the patient's past medical history may be prevented by providing cautions in the manner discussed above. For example, as shown in FIG. 7, a patient may be diagnosed by an orthopaedist that an X-ray imaging (e.g., CT imaging) is necessary and may move to a medical imaging lab for X-ray imaging. Next, a user of a CT imaging device (e.g., a medical imaging attendant or a medical technologist) performs a CT imaging on the patient. In this situation, the user may be provided with alarm information identifying a medical condition of the patient that is relevant with respect to performing CT imaging on the patient. For example, as shown in FIG. 12A, the alarm information 118a may include a text alert, such as "the patients is diabetic" or "the patient has previously received an arterial surgery." In addition, the alarm information 118a may include an image indicating that attention is required, such as an exclamation mark (!).

Furthermore, as shown in FIG. 12B, alarm information may be output via audio signals. For example, alarm information may be provided by a simple alarm sound like "beep" or by voices saying "the patients is diabetic" or "the patient has previously received an arterial surgery."

Furthermore, according to aspects of the present disclosure, the visual alarm information 118a as shown in FIG. 12A and acoustic alarm information 118b as shown in FIG. 12B may be provided to a user at the same time.

Furthermore, alarm information may include imaging guide information that may be provided to a patient. For example, the imaging guide information may include patient position correcting information (e.g., "Move to the right") or patient breathing information (e.g., "Take a deep breath and hold the breath for a while").

The guide information may be generated based on the patient information, and or any other type of information that is obtained based on the patient's identification information. For example, alarm information may be provided in one of various languages based on the patient information 114 including the nationality of a patient. For example, as shown in FIG. 12C, if nationality of a patient is Republic of Korea, breathing information 118 may be provided in Korean. Furthermore, if nationality of a patient is the United States of America, breathing information 118 may be provided in English. Furthermore, if nationality of a patient is Japan, breathing information 118 may be provided in Japanese.

Figure 13:
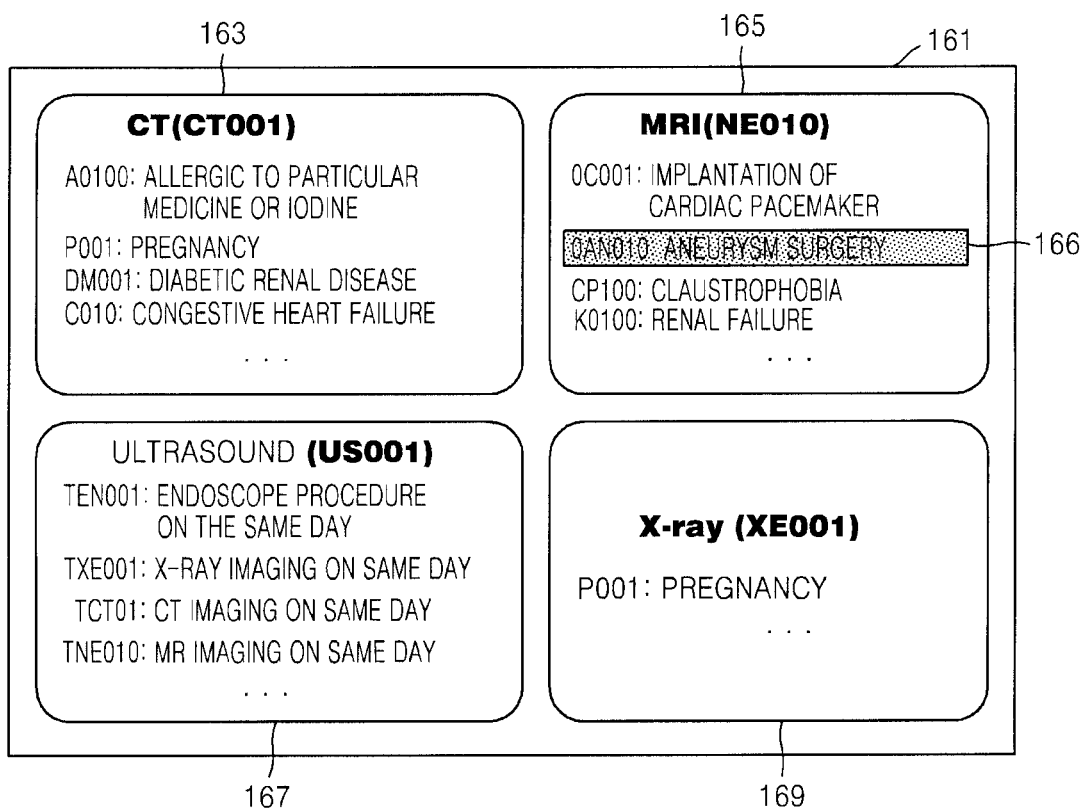
FIG. 13 is a diagram showing an example of a database 161 for storing different medical device alerts.

FIG. 13 is a diagram showing an example of a database 161 for storing different medical device alerts. As illustrated, the database 161 may include a plurality of records, with each record corresponding to a different medical device. For example, a record 163 for a CT imaging may include information regarding medicine allergies, contrast agent allergies, an indication of whether the patient is pregnant, diabetic renal disease, congestive heart failure, etc. A record 165 for a MRI imaging may include information regarding implants that are present in a patient's body (a cardiac pacemaker implant), past surgeries (e.g., an aneurysm surgery), psychological conditions (claustrophobia), past and present medical problems (e.g., renal failure, etc.). A record 167 for an ultrasound device may include information about other medical procedures that are performed or to be performed as part of the patient's current treatment (e.g., on the same day), such as information regarding an endoscope procedure, X-ray imaging, CT imaging on, MRI imaging, etc. Furthermore, a record 169 for an X-ray imaging device may include an indication of whether a patient is pregnant.

As illustrated, each record may be associated with a specific code identifying a particular medical device. For example, a code CT001 may be allocated to CT imaging. Furthermore, a code NE010 may be allocated to MRI imaging, a code US001 may be allocated to ultrasound, and a code XE001 may be allocated to X-ray imaging. Furthermore, each information item in the different database records may also be associated with a respective code. For example, a code A0100 may be used to denote medicine/iodine allergies, a code P001 may be used to denote pregnancy, a code DM001 may be used to denote diabetic renal disease, a code C010 for congestive heart failure, a code K0100 may be used to denote that the patient exhibits renal disorder symptoms, a code TEN001 may be used to denote that an endoscope procedure is performed or to be performed on the same day, a code TXE001 may be used to denote that X-ray imaging is performed or to be performed on the same day, a code TCT01 may be used to denote that CT imaging is performed or to be performed on the same day, and a code TNE010 may be used to denote that an MRI imaging is performed or to be performed on the same day. However, the present disclosure is not limited thereto.

For example, as shown in FIG. 7, if a patient has previously received a coronary artery surgery and an X-ray surgery imaging or an MRI imaging is necessary for observing development of herniation of an intervertebral disk, it may be determined whether information regarding an arterial surgery (e.g., information regarding a surgery at the coronary) included in the patient information 114 is part of an alert database record for MRI imaging and an alarm may be output if it is. In the present example, because the patient information 114 shown in FIG. 7 includes information regarding an arterial surgery OAN010 (e.g., information regarding a surgery at the coronary) and the record 165 for a MRI imaging NE010 shown in FIG. 13 indicates the arterial surgery OAN010, alarm information as shown in FIG. 12A may be provided to a user via code matching 166.

Figure 14:
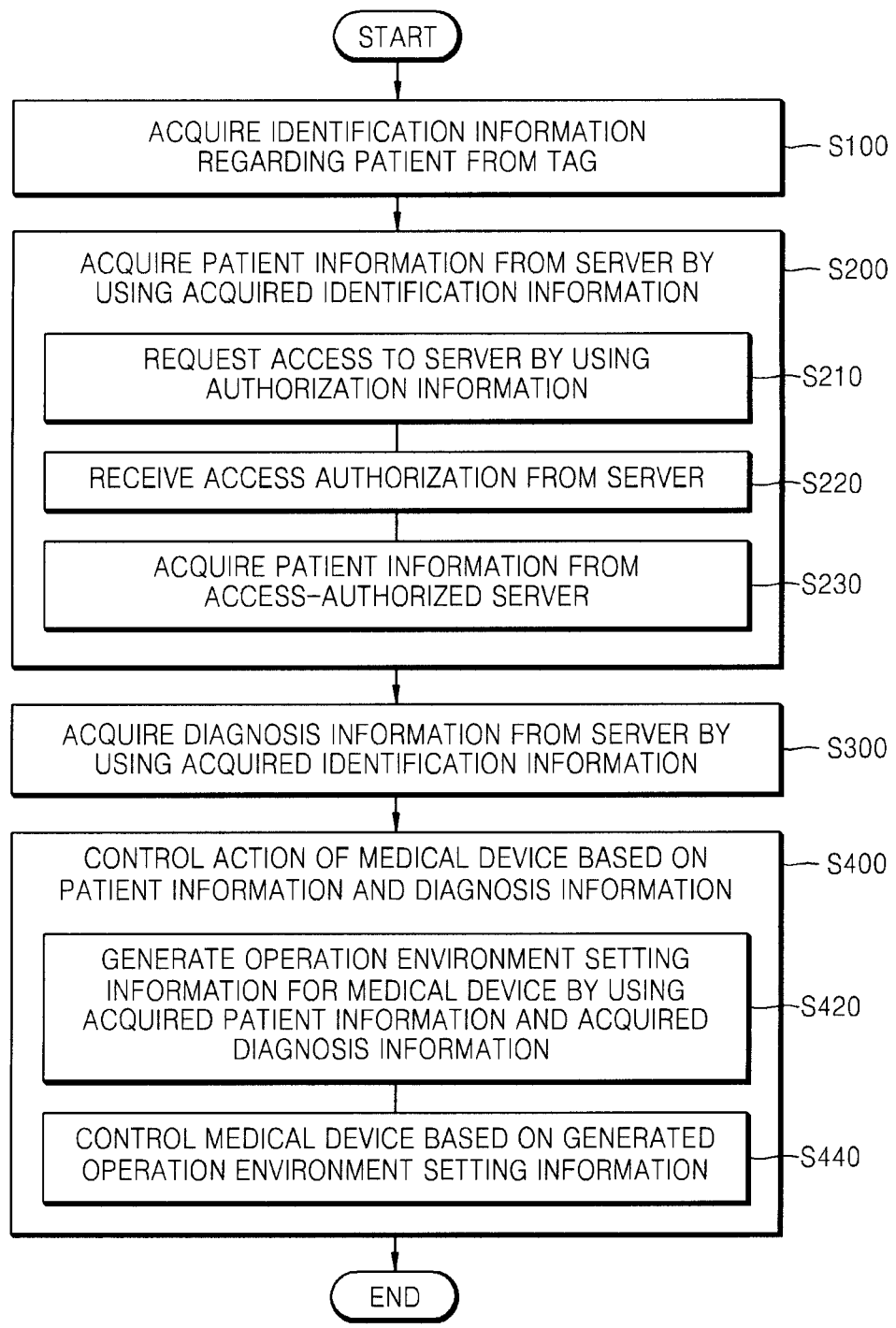
FIG. 14 is a flowchart illustrating another example of a process for performing operation S400 of the process of FIG. 3.

FIG. 14 is a flowchart illustrating another example of a process for performing operation S400 of the process of FIG. 3. At operation S420, operation environment setting information is generated for a particular medical device by using acquired patient information and acquired diagnostic information. At operation S440, the medical device is controlled based on the generated operation environment setting information. In some implementations, the operation environment setting information according to aspects of the present disclosure may include imaging protocols according to types of diagnosis.

Figure 15:
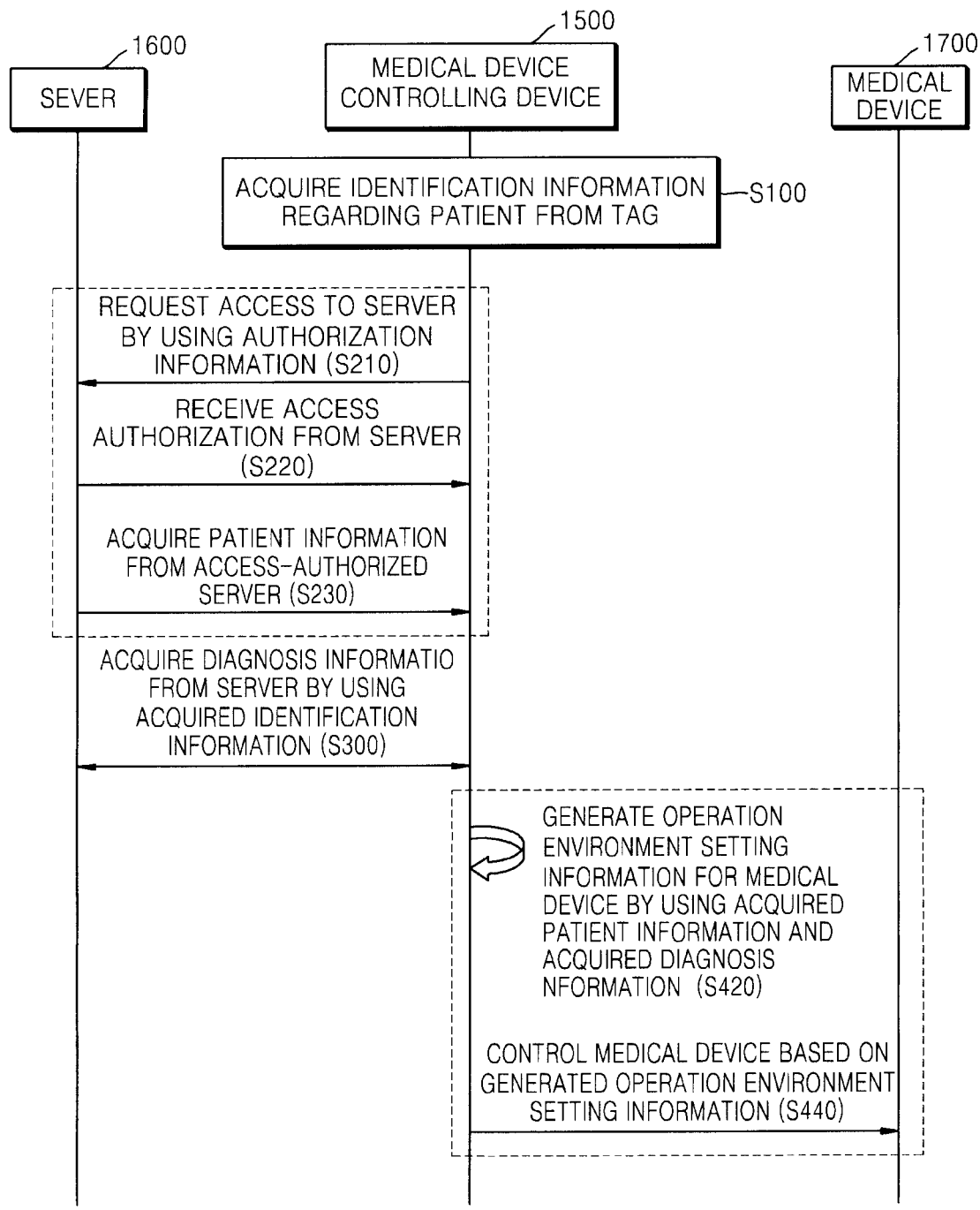
FIG. 15 is a flowchart illustrating an example of an implementation of the process of FIG. 14.

FIG. 15 is a flowchart illustrating an example of an implementation of the process of FIG. 14. As illustrated, the controlling device 1500 according to aspects of the present disclosure may generate operation environment setting information by using patient information and diagnostic information acquired from a server 1600 (operation S420). Furthermore, the controlling device 1500 may control a medical device 1700 based on the generated operation environment setting information (the operation S440).

FIGS. 16A through 16D are diagrams illustrating examples different changes of state that a medical device can undergo based on the patient information and/or the diagnostic information, according to aspects of the disclosure. Operation environment setting information according to aspects of the present disclosure may include an identification of at least one of a connector and a coil to be used during an imaging operation for a patient using a MRI device. Furthermore, the operation S440, in this example, may include displaying at least one from between a connector and a coil to be used based on the generated operation environment setting information.

Figure 16A:
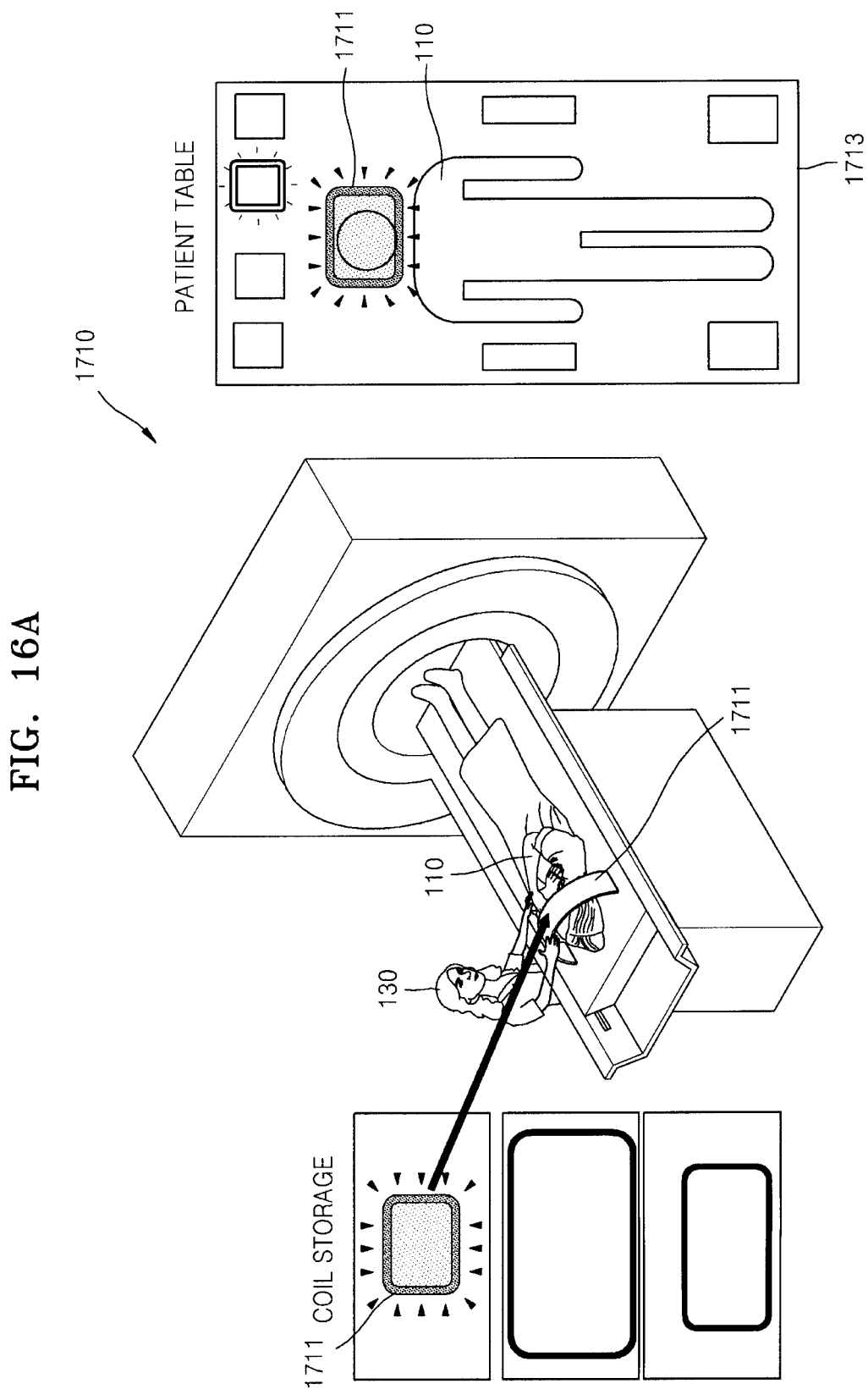

For example, in case of a patient 110 by using a MRI imaging device 1710 as shown in FIG. 16A, the MRI imaging device 1710 may be controlled based on operation environment setting information generated by using patient information and diagnostic information received form a server. For example, if a doctor desires to perform an MRI imaging on the head of a patient, a head coil 1711 stored in a coil storage may output an alarm or emit light based on patient information and diagnostic information, and thus a coil to be used for the MRI imaging may be indicated. The alarm may be output by a light source (e.g., LED) and/or a transducer that is located on the medical device, such as a light source and/or transducer located on the coil or coil storage. Therefore, a user may easily recognize that it is necessary to perform a MR image on the head of the patient. Furthermore, a connector at a patient table 1713 that needs to be connected to the head coil 1711 may produce an alarm or emit light, thereby making it more convenient for the user to use the medical device. Thus, in this example, the operation environment setting information may include an indication of a connector, coil, and or any other component of a medical device that is to be used on the patient.

Furthermore, in consideration of a body shape of a patient, height or horizontal location of the patient table 1713 may be automatically adjusted. Furthermore, based on age of a patient and development of symptom, X-ray dosage may be automatically adjusted. Furthermore, based on age of a patient and symptoms of the patient, moving speed of the patient table 1713 may differ. For example, moving speed of the patient table 1713 may be set to move slightly slower than normal speed for a senior citizen, a child, or a critical patient.

Thus, in this example, the operation environment setting information may include information identifying a desired location of a patient table, an X-ray dosage for the patient, etc.

Furthermore, the operation S440 for controlling the medical device based on the operation environment setting information generated in the operation S420 may include performing at least one of adjusting location of a patient table and adjusting X-ray dosage based on the generated operation environment setting information.

Figure 16B:
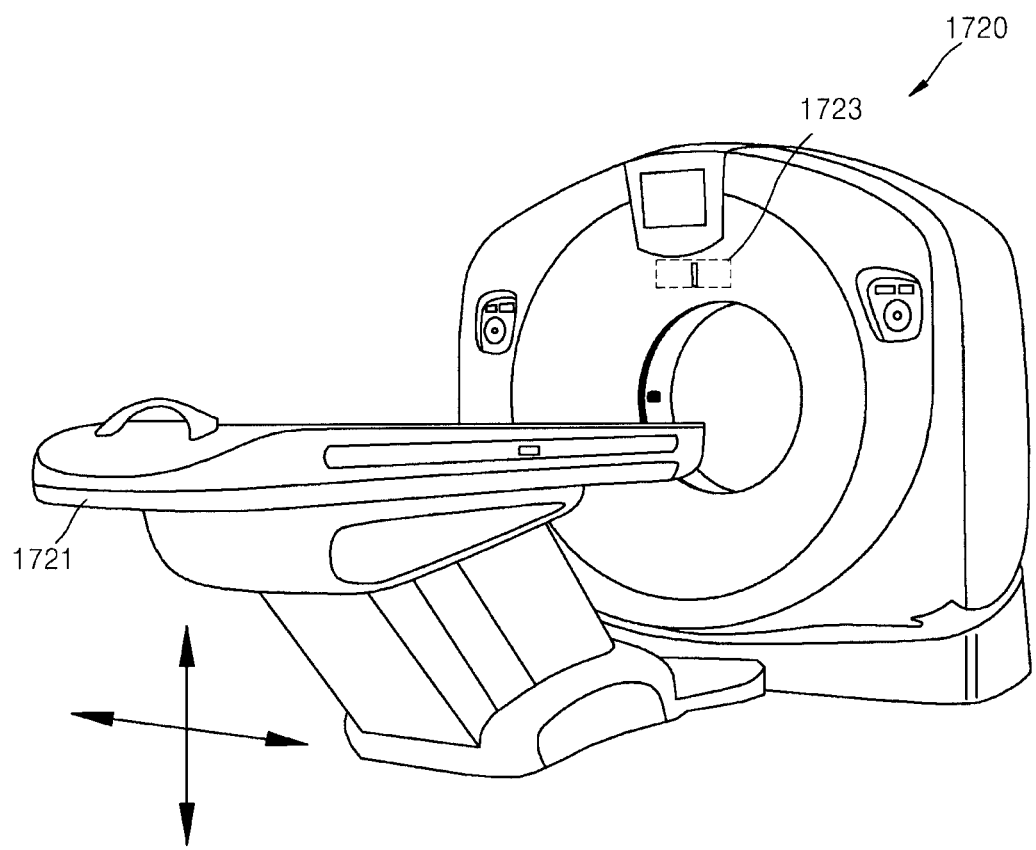

For example, as shown in FIG. 16B, to image a patient by using a CT device 1720, the CT device 1720 may be controlled based on operation environment setting information generated by using patient information and diagnostic information received from a server.

For example, in consideration of body shape of a patient, height or horizontal location of a patient table 1721 may be automatically adjusted. Furthermore, based on age of a patient and development of symptom, moving speed of the patient table 1721 may differ. For example, moving speed of the patient table 1721 may be set to move slightly slower than normal speed for a senior citizen, a child, or a critical patient.

Furthermore, based on age of a patient and/or a particular symptom that is exhibited by the patient and identified in the patient's identification and/or diagnosis information, X-ray dosage may be automatically adjusted. For example, X-ray dosage for a child patient may be adjusted to be smaller than that for an adult patient.

Figure 16C:
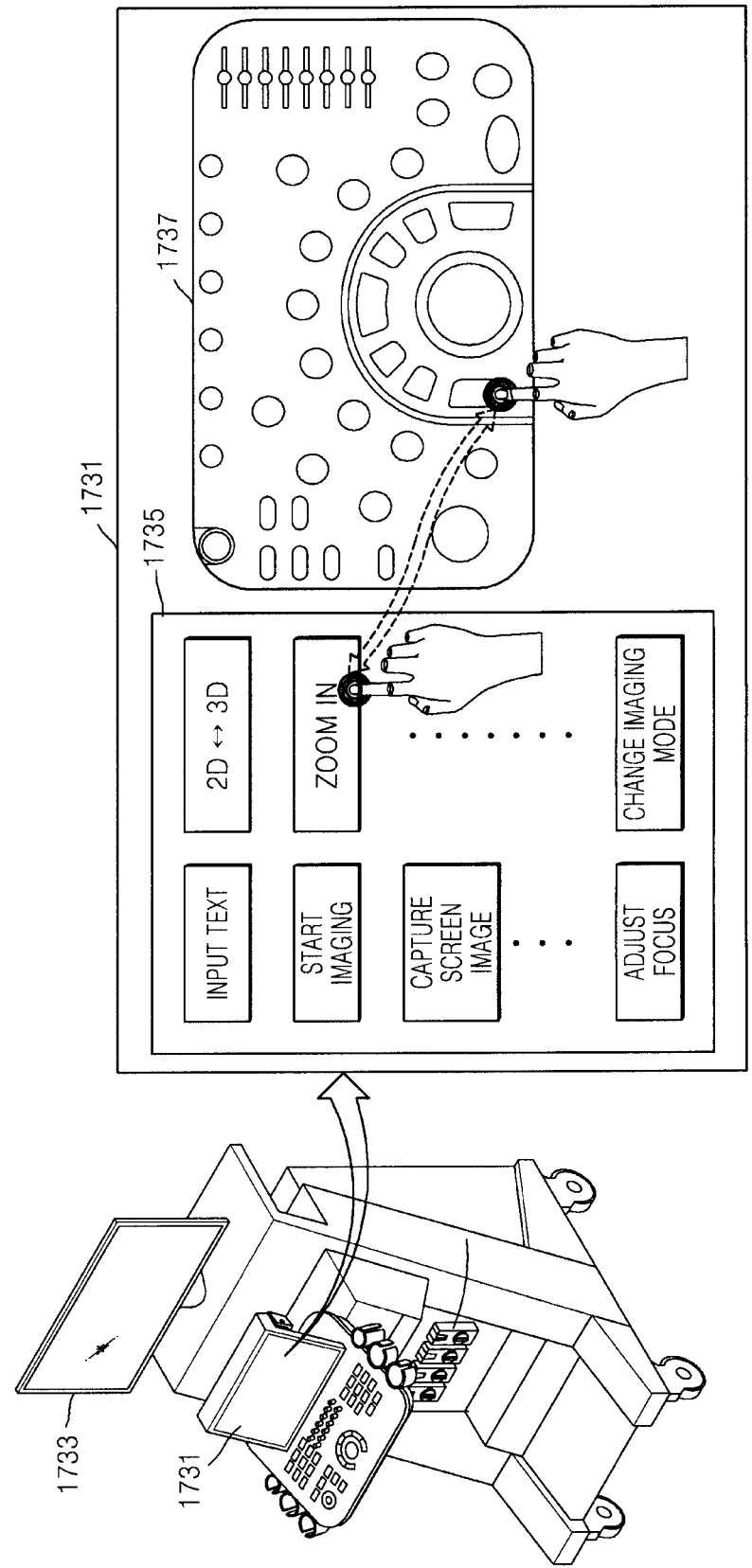

Operation environment setting information according to aspects of the present disclosure may include edit information for editing a UI according to imaging protocols of an ultrasound diagnosis device. In other words, if a medical device to be used is an ultrasound diagnosis device 1730 as shown in FIG. 16C, operation environment setting information may include edit information for editing a UI based on imaging protocols of the ultrasound diagnosis device 1730. The edit information for editing the UI may include at least one of a mapping between a particular function and a button (or another input component).

For example, areas for ultrasound diagnosis include the upper abdomen, the lower abdomen, the cervical portion, and the breast. Furthermore, functions of the ultrasound diagnosis device 1730 to be used for imaging the respective test areas may differ. Thus, in case of diagnosing the upper abdomen, an imaging mode switching function, an image zooming function, and a 2D-3D switching function of the ultrasound device may be mainly used. Meanwhile, in case of diagnosing the cervical portion, the image zooming function of ultrasound device may be used may be mainly used. In other words, since functions used for diagnosis of the upper abdomen differ from the function used for diagnosis of the cervical portion, the UI of the ultrasound device may be customized to the patient, such that at least one button indicating the imaging mode switching function, the image zooming function, and the 2D-3D switching function is moved from a first location to a second location in the user interface of the ultrasound device. Moving the button to the second location may place the button within easier reach by the user of the ultrasound device.

For example, as shown in FIG. 16C, UIs may be differently arranged on a control panel based on edit information. For instance, a UI may be edited based on external signals (e.g., drag-and-drop) for matching function information 1735 provided by a display component 1731 of the ultrasound diagnosis device 1730 with a control panel 1737.

Furthermore, the operation S440 for controlling the medical device based on the operation environment setting information generated in the operation S420 may include adjusting at least one from among location of a patient table, location of an X-ray source, location of a detector, and X-ray dosage based on the generated operation environment setting information.

For example, to image a patient by using an X-ray device 1740, the X-ray device 1740 may be controlled based on operation environment setting information generated by using patient information and diagnostic information received from a server.

As shown in FIG. 16D, for example, in consideration of body shape of a patient, height or horizontal location of a patient table 1745 may be automatically adjusted. Furthermore, based on age of a patient and development of symptom, moving speed of the patient table 1745 may differ. For example, moving speed of the patient table 1745 may be set to move slightly slower than normal speed for a senior citizen, a child, or a critical patient.

Furthermore, based on a body shape of a patient, locations of an X-ray source 1741 and a detector 1743 may be adjusted. The X-ray source 1741 or the detector 1743 may be relocated horizontally, vertically, or diagonally.

Furthermore, based on age of a patient and development of symptom, X-ray dosage from the X-ray source 1741 may be automatically adjusted. For example, X-ray dosage for a child patient may be adjusted to be smaller than that for an adult patient.

FIG. 17 is a flowchart of an example of a process for updating patient information according to aspects of the present disclosure. As illustrated, this process identical to the process of FIG. 3, but for containing an operation S500. At operation S500, a server is requested to update patient information based on acquired diagnostic information. By managing diagnostic information regarding a patient chronologically by updating patient information, medical history of the patient may be easily tracked and managed, and information regarding the patient may be maintained up-to-date. A user may improve precision of diagnosis regarding the patient by using the updated patient information.

FIG. 18 is a diagram of an example of the controlling device 1500 according to aspects of the present disclosure. In this example, the controlling device includes an identification information acquiring unit 1510 for acquiring identification information regarding a patient from a tag, a patient information acquiring unit 1530 for acquiring patient information from a server by using the acquired identification information, a diagnostic information acquiring unit 1550 for acquiring diagnostic information from a server by using the acquired identification information, and a control unit 1570 for controlling an action of a medical device based on the patient information and diagnostic information.

Furthermore, as shown in FIG. 18, the controlling device 1500 may include a communication unit 1810, an output unit 1830, a user input unit 1850, and a memory 1870. However, not all of the components shown in FIG. 18 are necessary. The controlling device 1500 may be implemented with fewer or more components than those shown in FIG. 18.

The communication unit 1810 may include one or more components enabling communication between the controlling device 1500 and the server 1600 and between the controlling device 1500 and the medical device 1700. For example, the communication unit 1810 may include a wireless communication unit, a close-distance communication unit, and a wired communication unit.

The communication unit 1810 may perform a wireless communication with the server 1600 or the medical device 1700 via the wireless communication unit. In other words, wireless signals may be transmitted and received to and from at least one of a station, a terminal, and a server on a wireless communication network via the wireless communication unit. Here, the wireless signals may include voice call signals, video call signal, or various types of data regarding transmission and reception of text/multimedia messages.

Furthermore, the communication unit 1810 may support close-distance communication techniques other than wireless communication. Examples of close-distance communication techniques according to aspects of the present disclosure may include Wi-Fi, Bluetooth, Zigbee, Wi-Fi Direct (WFD), ultra wideband (UWB), or infrared data association (IrDA). However, the present disclosure is not limited thereto.

Furthermore, the communication unit 1810 may perform a wired communication with the server 1600 or the medical device 1700 via the wired communication unit. In other words, the communication unit 1810 may exchange data with other devices (e.g., mobile devices, servers, etc.) connected via a conventional telephone cable, a modem, a carrier-frequency cable, a coaxial cable, or an optical fiber on a communication network.

The output unit 1830 is a unit for outputting audio signals, video signals, or oscillation signals. The output unit 1830 may include a display unit, an acoustic output unit, and an alarm unit.

The display unit may process and display information processed by the controlling device 1500. For example, the display unit may display a UI or a GUI related to patient information or diagnostic information of a patient.

Furthermore, the display unit may display a UI or a GUI related to actions of the medical device 1700 and may display a captured image when the medical device 1700 is in an imaging mode.

Meanwhile, if the display unit and a touch pad constitute a layered structure and are configured as a touch screen, the display device may be used not only as an output device, but also as an input device. The display unit may include at least one from among a liquid crystal display (LCD), a thin-film transistor (TFT) LCD, an organic light-emitting diode, a flexible display, a 3D display, and an electrophoretic display.

Furthermore, according to embodiments of the controlling device 1500, the controlling device 1500 may include at least one display unit. Moreover, in some implementations, a plurality of display units may be arranged in a lattice-shape. However, the present disclosure is not limited thereto.

The acoustic output unit may output audio data received from the communication unit 1810 or stored in the memory 1870. Furthermore, the acoustic output unit outputs acoustic signals related to functions performed by the controlling device 1500 (e.g., relocation of a medical device, information message, etc.). The acoustic output unit may include a speaker, a buzzer, etc.

The alarm unit may generate signals for informing occurrence of an event at the controlling device 1500. Examples of event that occurs at the controlling device 1500 may include data transmission or reception, input of an external signal, transmission of alarm message, etc.

The alarm unit may include a vibration motor for outputting vibrations, a light emitting device for emitting light alerts, etc. For example, the alarm unit may output oscillation signals corresponding to audio data or video data (e.g., alarm message). Furthermore, the alarm unit may output light signals corresponding to audio data or video data (e.g., alarm message). Furthermore, the vibration motor may output vibrations when a touch is input to a touch screen.

Furthermore, the alarm unit may provide snooze function. For example, if a user sets the number of alarm repetitions (e.g., 5 times) or an interval for alarm repetitions (e.g., 3 minutes), the alarm unit may output alarm signals for a predetermined number of times (e.g., 5 times) or at a predetermined interval (e.g., 3 minutes).

A user input unit 1850 may include key pads, dome switches, touch pads (capacitive overlay type, resistive overlay type, infrared beam type, integral strain gauge type, surface acoustic wave type, piezoelectric type, etc.), jog wheels, and jog switches. However, the present disclosure is not limited thereto.

The user input unit 1850 may receive an input for controlling the medical device 1700 from a user of the controlling device 1500. The user input unit 1850 according to aspects of the present disclosure may receive a plurality of inputs regarding the medical device 1700 on the time basis. The memory 1870 according to aspects of the present disclosure may store a program for performing processes at the control unit 1570 or for controlling the control unit 1570 or may store input/output data (e.g., identification information, patient information, and diagnostic information). The memory 1870 may include at least one from among a flash memory type memory, a hard disk type memory, a multimedia card micro type memory, a card type memory (e.g., a SD memory or a XD memory), a random access memory (RAM), a static RAM (SRAM), a read-only memory (ROM), an electronically erasable/programmable ROM (EEPROM), a programmable ROM (PROM), a magnetic memory, a magnetic disk, and an optical disc. Furthermore, the controlling device 1500 may operate a web storage which functions as the user input unit 1850 on the internet.

The user input unit 1850 may include a voice recognition module (not shown), which recognizes voice of a user by using a voice recognition engine and transmits the recognized voice to the control unit 1570.

Figure 19:
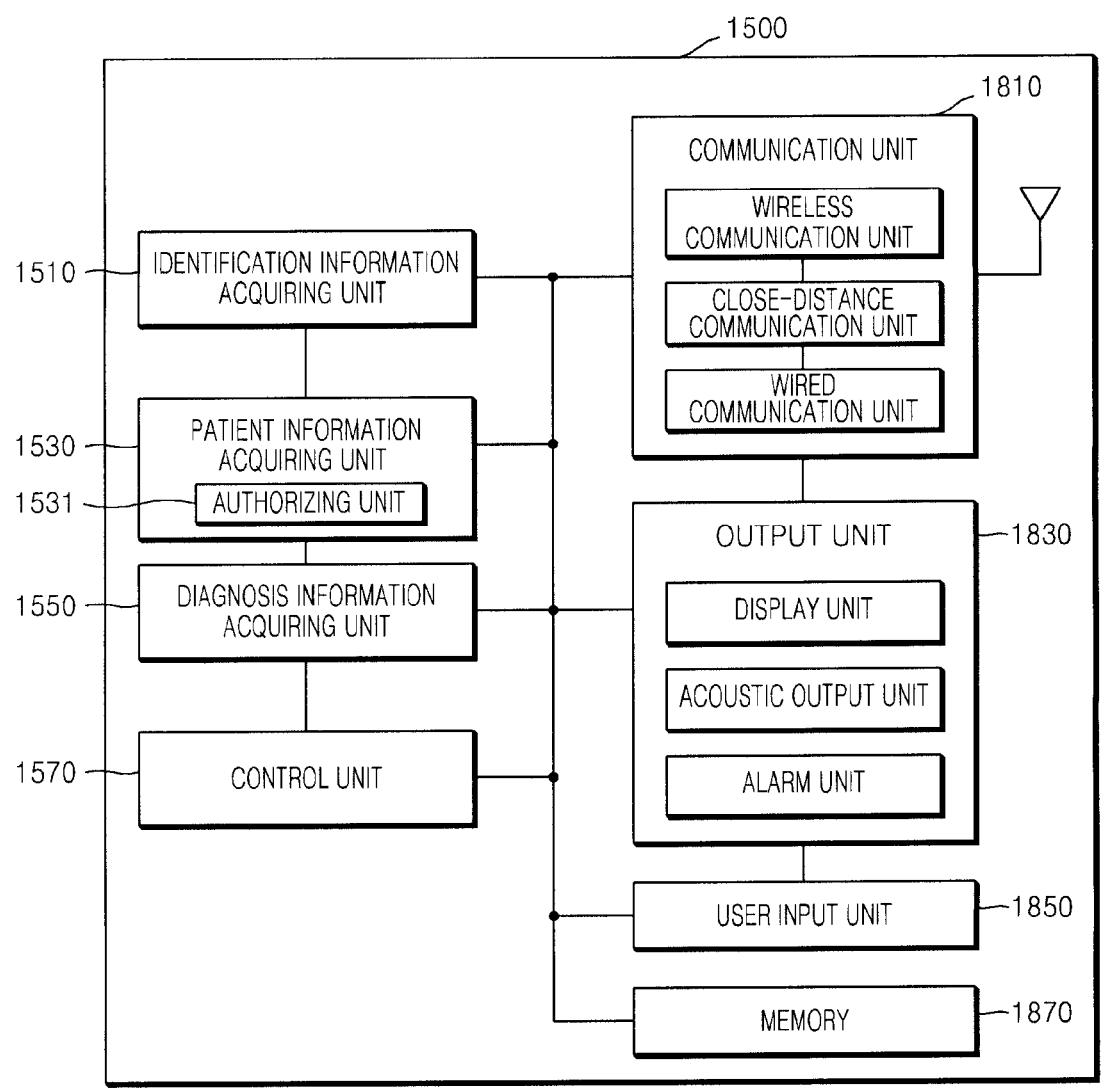
FIG. 19 is a diagram of the controlling device showing the controlling device's patient information acquiring unit in further detail.

FIG. 19 is a diagram of the controlling device 1500 showing the patient information acquiring unit 1530 in further detail. As illustrated, the patient information acquiring unit 1530 may further include an authorizing unit 1531, which requests an access to a server by using authorization information and receives an access authorization from the server.

Figure 20:
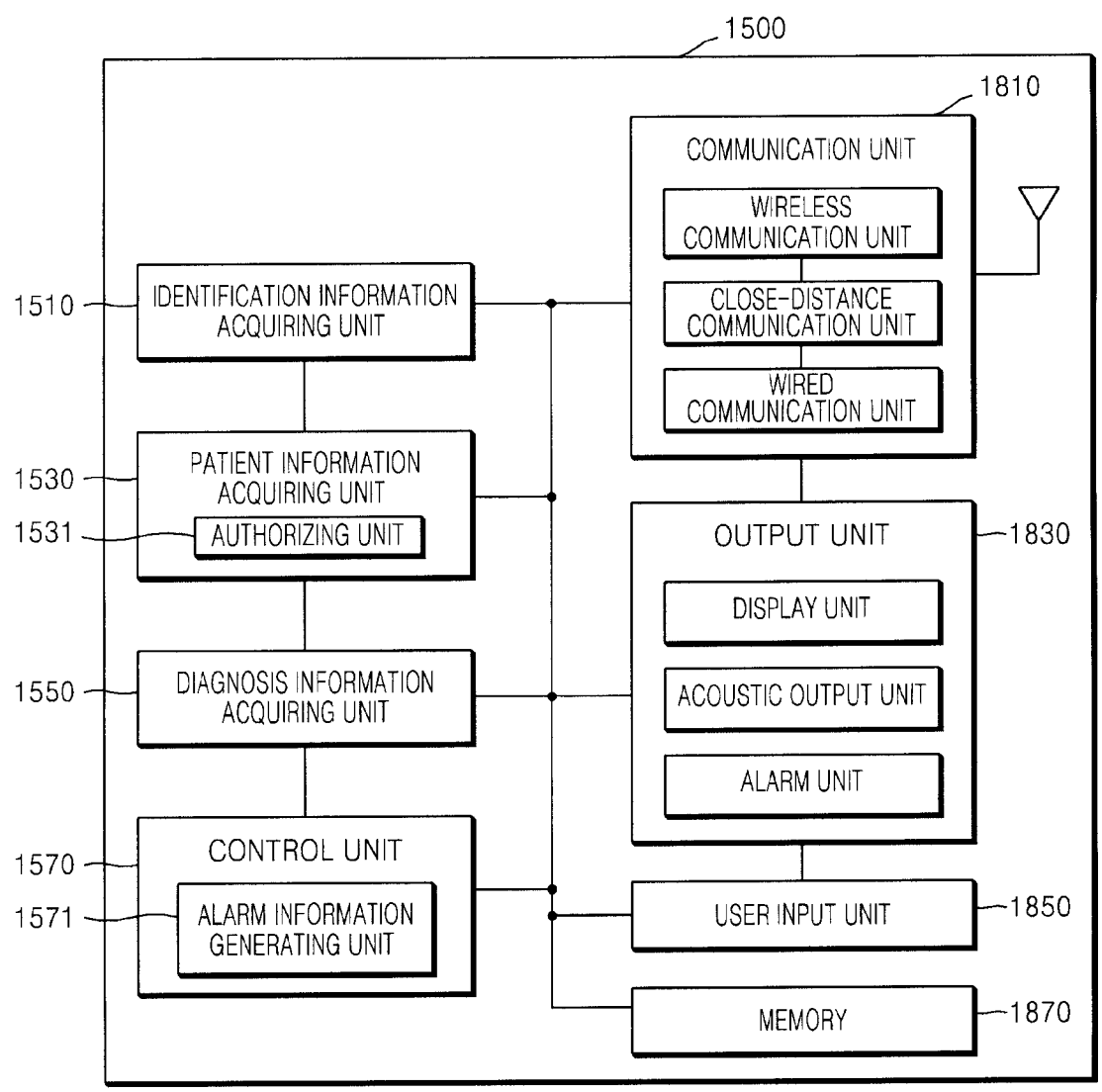
FIG. 20 is a diagram of the controlling device showing the controlling device's control unit in further detail.

FIG. 20 is a diagram of the controlling device 1500 showing the control unit 1570 in further detail. The control unit 1570 according to aspects of the present disclosure may further include an alarm information generating unit 1571 which generates predetermined alarm information by using acquired patient information and diagnostic information.

Figure 21:
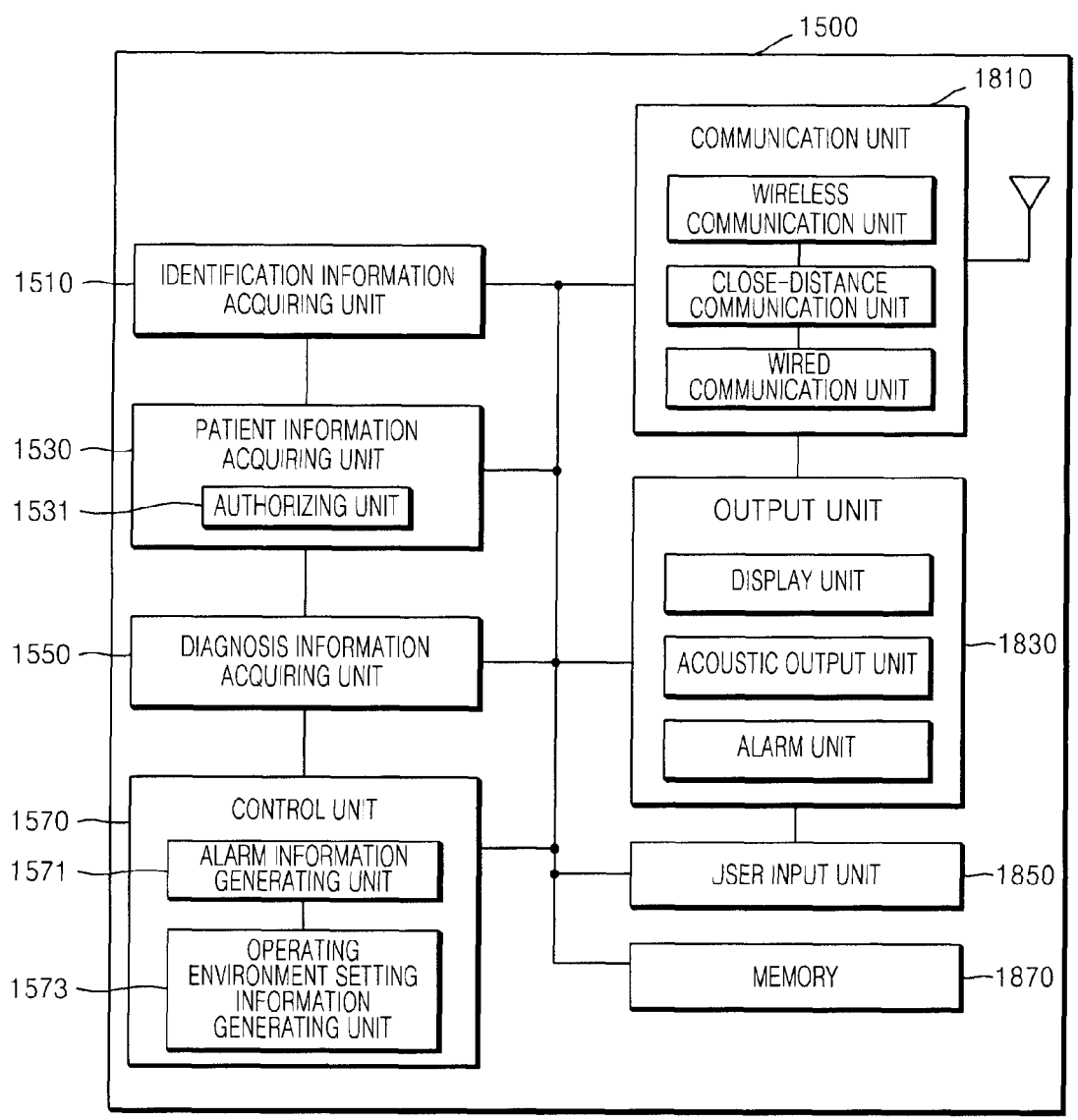
FIG. 21 is another diagram of the controlling device showing the controlling device's control unit in further detail.

FIG. 21 is a diagram of the controlling device 1500 showing the control unit 1570 in further detail. The control unit 1570 according to this example may further include an operating environment setting information generating unit 1573, which generates operation environment setting information regarding the medical device 1700 by using acquired patient information and diagnostic information.

Furthermore, the control unit 1570 may control the medical device 1700 based on the generated operation environment setting information.

Operation environment setting information according to aspects of the present disclosure may include information regarding at least one from between a connector and a coil to be used for imaging a patient using a MRI device.

The control unit 1570 according to aspects of the present disclosure may display an indication of at least one of a connector and a coil to be used for imaging a patient using a MRI device based on the generated operation environment setting information.

Operation environment setting information according to aspects of the present disclosure may include information regarding at least one of a patient table and X-ray dosage for imaging a patient using a CT device.

Furthermore, the control unit 1570 may perform at least one of adjusting location of a patient table and adjusting X-ray dosage based on the generated operation environment setting information.

Operation environment setting information according to aspects of the present disclosure may include edit information for editing a UI according to imaging protocols of an ultrasound diagnosis device.

The control unit 1570 according to aspects of the present disclosure may edit a UI of an ultrasound diagnosis device based on generated edit information.

Operation environment setting information according to aspects of the present disclosure may include information regarding at least one from among location of a patient table, location of an X-ray source, location of a detector, and X-ray dosage for imaging a patient by using an X-ray device.

Furthermore, the control unit 1570 may adjust at least one from among location of a patient table, location of an X-ray source, location of a detector, and X-ray dosage based on the generated operation environment setting information.

Figure 22:
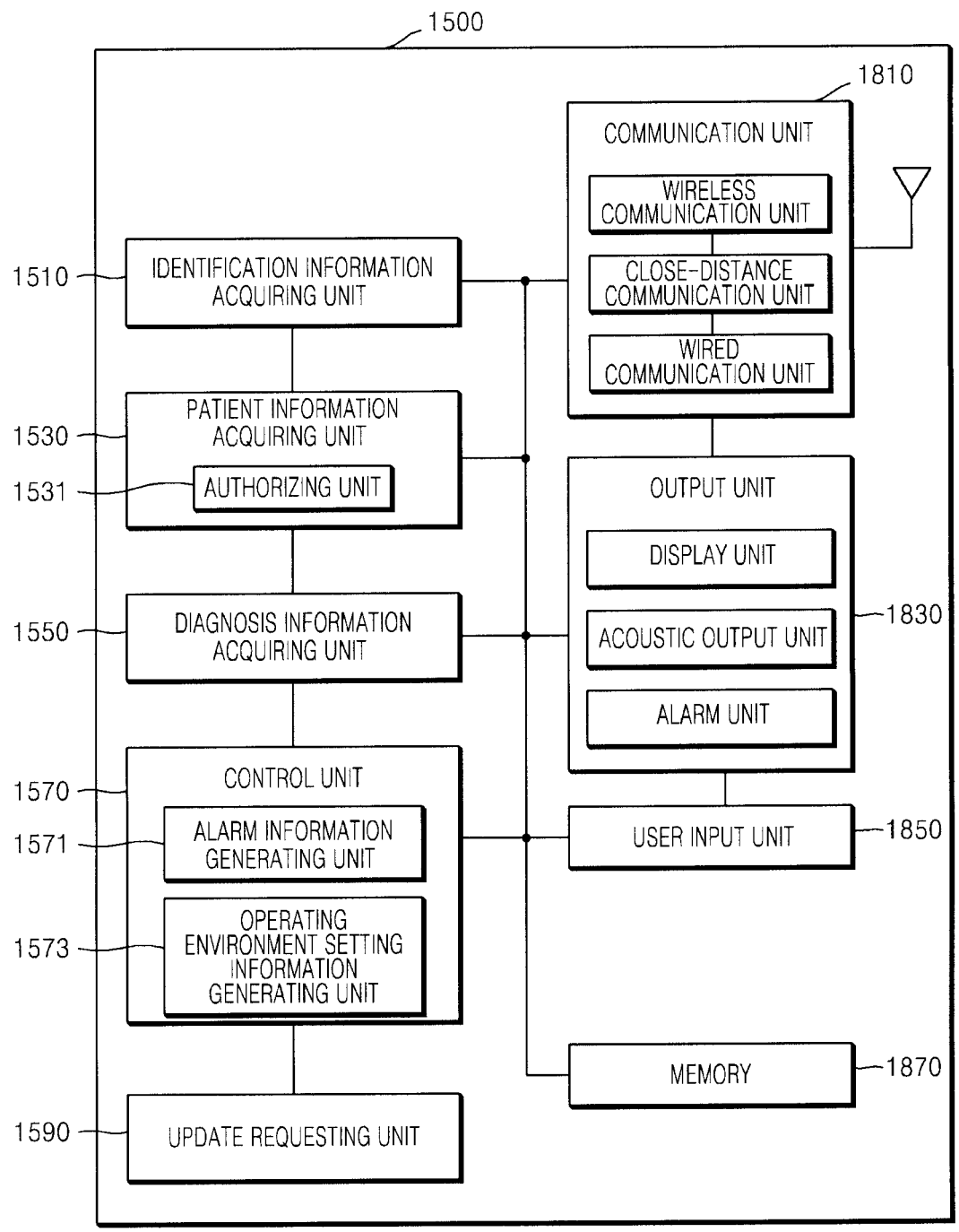
FIG. 22 is another diagram of an example of a controlling device, according to aspects of the present disclosure.

FIG. 22 is a block diagram of the controlling device 1500 in accordance with another example. In this example, the controlling device 1500 includes an update requesting unit 1590, which requests the server 1600 to update patient information based on acquired diagnostic information.

The above-described aspects of the present disclosure can be implemented in hardware, firmware or via the execution of software or computer code that can be stored in a recording medium such as a CD ROM, a Digital Versatile Disc (DVD), a magnetic tape, a RAM, a floppy disk, a hard disk, or a magneto-optical disk or computer code downloaded over a network originally stored on a remote recording medium or a non-transitory machine readable medium and to be stored on a local recording medium, so that the methods described herein can be rendered via such software that is stored on the recording medium using a general purpose computer, or a special processor or in programmable or dedicated hardware, such as an ASIC or FPGA. As would be understood in the art, the computer, the processor, microprocessor controller or the programmable hardware include memory components, e.g., RAM, ROM, Flash, etc. that may store or receive software or computer code that when accessed and executed by the computer, processor or hardware implement the processing methods described herein. In addition, it would be recognized that when a general purpose computer accesses code for implementing the processing shown herein, the execution of the code transforms the general purpose computer into a special purpose computer for executing the processing shown herein. Any of the functions and steps provided in the Figures may be implemented in hardware, software configured into hardware or a combination of both and may be performed in whole or in part within the programmed instructions of a computer. No claim element herein is to be construed under the provisions of 35 U.S.C. 112, sixth paragraph, unless the element is expressly recited using the phrase "means for".

What is claimed is:

1. A method for controlling a medical device, the method comprising:
    acquiring identification information of a patient;
    acquiring patient information and diagnostic information based on the identification information; and
    changing a state of the medical device based on the patient information and the diagnostic information, wherein the changing of the state of the medical device includes moving a physical component of the medical device to a position that is selected by a control unit based on the patient information and the diagnostic information.

2. The method of claim 1, wherein the identification information is acquired from a tag capable of performing close distance communications.

3. The method of claim 1, wherein the identification information is acquired by using at least one of iris recognition, face recognition, fingerprint recognition, and voice recognition.

4. The method of claim 1, wherein the patient information and the diagnostic information are acquired from a server comprising at least one of a picture archiving and communication system (PACS), an electronic medical record (EMR), a personal health record (PHR), and a radiology information system (RIS).

5. The method of claim 1, wherein the patient information and the diagnostic information are acquired from a server comprising a cloud server.

6. The method of claim 1, wherein the patient information includes at least one of a name, age, gender, body measures, diagnosis history, and current symptom of the patient.

7. The method of claim 1, wherein:
    the identification information further comprises authorization information, and
    the acquiring of the patient information comprises: requesting an access to a server by using the authorization information, receiving an access authorization from the server, and receiving the patient information from the server.

8. The method of claim 1, wherein the changing of the state of the medical device comprises:
    generating an alarm; and
    outputting the alarm by the medical device.

9. The method of claim 8, wherein the alarm includes a message that is based on a medical condition identified in the diagnostic information.

10. The method of claim 1, wherein changing the state of the medical device comprises generating operation environment setting information for the medical device by using the patient information and the diagnostic information, wherein the state of the medical device is changed based on the operation environment setting information.

11. The method of claim 10, wherein the operation environment setting information includes a configuration setting of a patient table.

12. The method of claim 10, wherein:
    the operation environment setting information comprises an indication of the position, and
    the physical component of the medical device includes at least one of a patient table, an X-ray source, and a detector.

13. The method of claim 1, wherein changing the state of the medical device further includes turning on a visual indicator disposed next to an input component of the medical device, the input component being one that is to be physically manipulated as part of using the medical device on the patient.

14. The method of claim 1, further comprising requesting a server to update the patient information.

15. An apparatus for controlling a medical device, the apparatus comprising:
    an identification information acquiring unit for acquiring identification information of a patient from a tag;
    a patient information acquiring unit for acquiring patient information from a server, the patient information being acquired based on the identification information;
    a diagnostic information acquiring unit for acquiring diagnostic information for the patient from the server, the diagnostic information being acquired based on the identification information; and
    a control unit for changing a state of the medical device based on the patient information and the diagnostic information, wherein the changing of the state of the medical device includes moving a physical component of the medical device to a position that is selected by the control unit based on the patient information and the diagnostic information.

16. The apparatus of claim 15, wherein the identification acquiring unit is capable of performing close distance communications.

17. The apparatus of claim 15, wherein the identification information is acquired by using at least one of iris recognition, face recognition, fingerprint recognition, and voice recognition.

18. The apparatus of claim 15, wherein the server comprises at least one of a picture archiving and communication system (PACS), an electronic medical record (EMR), a personal health record (PHR), and a radiology information system (RIS).

19. The apparatus of claim 15, wherein the server comprises a cloud server.

20. The apparatus of claim 15, wherein:
the patient information includes at least one of a name, age, gender, body measures, diagnosis history, and current symptom of the patient.

21. The apparatus of claim 15, wherein:
the identification information further comprises authorization information, and
the acquiring of the patient information comprises: requesting an access to the server by using the authorization information, receiving an access authorization from the server, and receiving the patient information from the server.

22. The apparatus of claim 15, wherein the changing of the state of the medical device comprises:
generating an alarm; and
outputting the alarm by the medical device.

23. The apparatus of claim 22, wherein the alarm includes a message that is based on a medical condition identified in the diagnostic information.

24. The apparatus of claim 15, wherein changing the state of the medical device comprises generating operation environment setting information for the medical device by using the patient information and the diagnostic information, wherein the state of the medical device is changed based on the operation environment setting information.

25. The apparatus of claim 24, wherein changing the state of the medical device comprises turning on a visual indicator disposed next to an input component of the medical device, the input component being one that is to be physically manipulated as part of using the medical device on the patient.

26. The apparatus of claim 24, wherein:
the operation environment setting information comprises includes a configuration setting of a patient table.

27. The apparatus of claim 24, wherein:
the operation environment setting information comprises an indication of the position, and
the physical component of the medical device includes at least one of a patient table, an X-ray source, and a detector.

28. The apparatus of claim 15, further comprising an update requesting unit for requesting the server to update the patient information.

29. A method for controlling a medical device, the method comprising:
acquiring identification information of a patient;
acquiring patient information and diagnostic information based on the identification information; and
changing a state of the medical device based on the patient information and the diagnostic information,
wherein changing the state of the medical device comprises generating operation environment setting information for the medical device by using the patient information and the diagnostic information, wherein the state of the medical device is changed based on the operation environment setting information
wherein the operation environment setting information includes edit information for editing a graphical user interface (GUI) of the medical device, and
changing the state of the medical device further includes modifying the GUI of the medical device based on the edit information.

30. An apparatus for controlling a medical device, the apparatus comprising:
an identification information acquiring unit for acquiring identification information of a patient from a tag;
a patient information acquiring unit for acquiring patient information from a server, the patient information being acquired based on the identification information;
a diagnostic information acquiring unit for acquiring diagnostic information for the patient from the server, the diagnostic information being acquired based on the identification information; and
a control unit for changing a state of the medical device based on the patient information and the diagnostic information,
wherein changing the state of the medical device comprises generating operation environment setting information for the medical device by using the patient information and the diagnostic information, wherein the state of the medical device is changed based on the operation environment setting information, and
wherein the operation environment setting information comprises edit information for editing a graphical user interface (GUI) of the medical device, and changing the state of the medical device includes modifying the GUI of the medical device based on the edit information.

* * * * *

UNITED STATES PATENT AND TRADEMARK OFFICE
CERTIFICATE OF CORRECTION

PATENT NO. : 9,098,861 B2  
APPLICATION NO. : 14/310657  
DATED : August 4, 2015  
INVENTOR(S) : Dae-hyun Ban et al.

Page 1 of 1

It is certified that error appears in the above-identified patent and that said Letters Patent is hereby corrected as shown below:

In the Claims,

Column 19, Claim 26, Lines 32-33 should read as follows:
--...information comprises a configuration...--

Column 20, Claim 29, Lines 10-11 should read as follows:
--...setting information, wherein the...--

Signed and Sealed this
Eighth Day of December, 2015

Michelle K. Lee
*Director of the United States Patent and Trademark Office*